US007780593B2

(12) United States Patent
Ueno et al.

(10) Patent No.: US 7,780,593 B2
(45) Date of Patent: Aug. 24, 2010

(54) ENDOSCOPE

(75) Inventors: Haruhiko Ueno, Akiruno (JP); Yuichi Ikeda, Tama (JP); Tomoaki Sato, Higashiyamato (JP); Shuji Nakamura, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 253 days.

(21) Appl. No.: 11/963,915

(22) Filed: Dec. 24, 2007

(65) Prior Publication Data

US 2008/0125628 A1 May 29, 2008

Related U.S. Application Data

(63) Continuation of application No. PCT/JP2006/311117, filed on Jun. 2, 2006.

(30) Foreign Application Priority Data

Jun. 24, 2005 (JP) ............................. 2005-184967

(51) Int. Cl.
*A61B 1/00* (2006.01)
*A61B 1/01* (2006.01)
(52) U.S. Cl. ...................... 600/146; 600/130; 600/139
(58) Field of Classification Search ......... 600/139–142, 600/146–150, 130, 131
See application file for complete search history.

(56) References Cited

U.S. PATENT DOCUMENTS

| 3,892,228 | A | * | 7/1975 | Mitsui | 600/149 |
| 4,203,430 | A | * | 5/1980 | Takahashi | 600/149 |
| 4,207,873 | A | * | 6/1980 | Kruy | 600/146 |
| 4,718,407 | A | * | 1/1988 | Chikama | 600/150 |
| 4,721,099 | A | * | 1/1988 | Chikama | 600/152 |
| 4,919,112 | A | * | 4/1990 | Siegmund | 600/136 |
| 4,982,725 | A | * | 1/1991 | Hibino et al. | 600/117 |
| 5,179,935 | A | * | 1/1993 | Miyagi | 600/142 |
| 5,359,994 | A | * | 11/1994 | Krauter et al. | 600/149 |
| 5,388,568 | A | * | 2/1995 | van der Heide | 600/146 |
| 5,531,686 | A | * | 7/1996 | Lundquist et al. | 604/95.04 |
| 5,549,542 | A | * | 8/1996 | Kovalcheck | 600/146 |
| 5,667,476 | A | * | 9/1997 | Frassica et al. | 600/149 |
| 6,171,277 | B1 | * | 1/2001 | Ponzi | 604/95.04 |
| 7,008,376 | B2 | * | 3/2006 | Ikeda et al. | 600/152 |

FOREIGN PATENT DOCUMENTS

| JP | 7-116104 | 5/1995 |
| JP | 2000-014628 | 1/2000 |

* cited by examiner

*Primary Examiner*—John P Leubecker
*Assistant Examiner*—Victoria W Chen
(74) *Attorney, Agent, or Firm*—Scully, Scott, Murphy & Presser, P.C.

(57) ABSTRACT

A bend section is disposed on an insertion section. A rotary body, on which a proximal end portion of a wire for a bend operation, which has a distal end portion connected to the bend section, is rotatably supported in a large-diameter section. Driving force transmission portion, which converts linear movement of a working shaft that is operable in a linear direction to rotational movement of the rotary body, is provided in the large-diameter section. A driving source unit is detachably coupled to the large-diameter section on the proximal end side of the insertion section. The driving source unit is provided with operation section which linearly moves the working shaft, in accordance with an operation of a driving shaft that operates in a linear direction by a driving force from a driving motor.

6 Claims, 12 Drawing Sheets

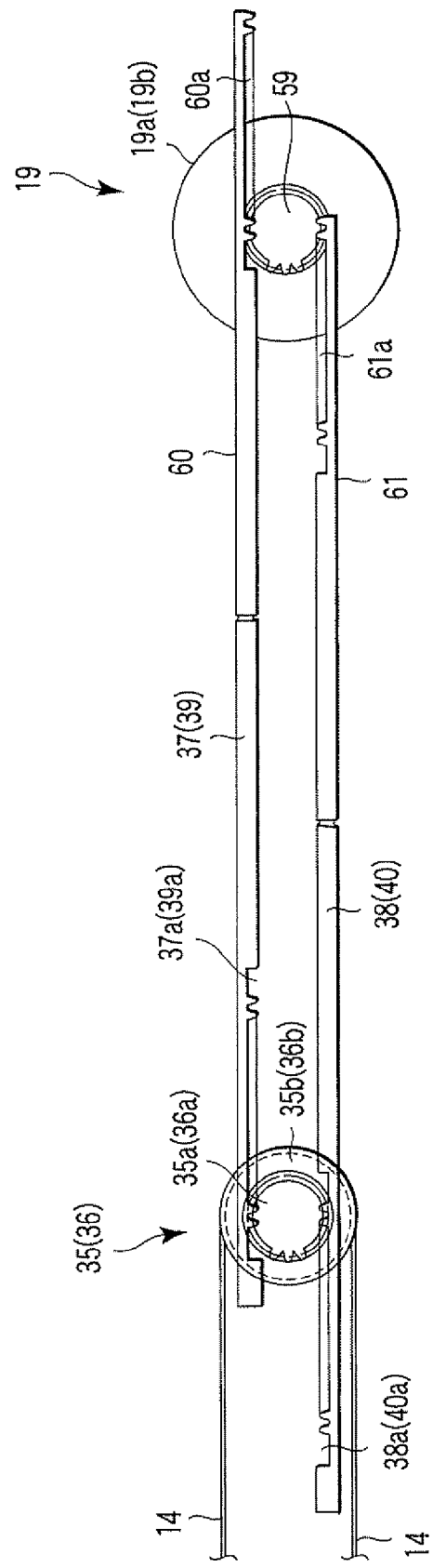
F I G. 6B

ENDOSCOPE

CROSS-REFERENCE TO RELATED APPLICATIONS

This is a Continuation Application of PCT Application No. PCT/JP2006/311117, filed Jun. 2, 2006, which was published under PCT Article 21(2) in Japanese.

This application is based upon and claims the benefit of priority from prior Japanese Patent Application No. 2005-184967, filed Jun. 24, 2005, the entire contents of which are incorporated herein by reference.

BACKGROUND OF THE INVENTION

1. Field of the Invention

The present invention relates to an endoscope of a type in which a driving source unit is attachable/detachable. The endoscope includes a driving source unit which incorporates driving force generating means for bend-operating a bend section that is disposed at a distal end side of an insertion section of the endoscope. The driving source unit is detachably attached to a proximal end portion of the insertion section via an attachment/detachment section.

2. Description of the Related Art

Jpn. Pat. Appln. KOKAI Publication No. 2000-014628 (Patent Document 1) discloses an endoscope apparatus which is configured such that an insertion section of an endoscope and a proximal-end-side operation section, which is disposed at a proximal end portion of the insertion section, are detachably coupled via an attachment/detachment section. In the insertion section of the endoscope, a bend section, which is bendable, is provided between an elongated soft portion and a distal end portion. An operation knob of a bend operation mechanism, which bend-operates the bend section, is provided on the operation section side.

In addition, four wire cables for bend-operating the bend section are inserted in the insertion section. Distal end portions of the four wire cables are fixed to a distal end portion of the bend section. Proximal end portions of the wire cables extend toward the proximal end portion of the insertion section. A transmission mechanism for transmitting a driving force, which is transmitted from the operation knob, to the bend section, is provided on the proximal end side of the insertion section. The transmission mechanism includes guide wheels for reversing the directions of the four wire cables, and driven shafts. The proximal end portions of the wire cables are coupled to the driven shafts via the guide wheels.

A pinion is fixed to a driving shaft of the operation knob of the operation section. The pinion is provided with a pair of racks which are disposed to be opposed to each other. The pinion and the paired racks are held in a meshed state. In addition, driving shafts are coupled to the racks. When the proximal end portion of the insertion section of the endoscope is coupled to the operation section via the attachment/detachment section, the driving shafts and the driven shafts are abutted upon each other, and the bend operation is performed by advancing and retreating the driven shafts.

BRIEF SUMMARY OF THE INVENTION

According to a first aspect of the present invention, there is provided an endoscope comprising: an insertion section which is insertable in a body cavity; a bend section which is disposed on a distal end side of the insertion section and is constituted by coupling a plurality of bend pieces; a wire for a bend operation of the bend section, which has a distal end portion connected to the bend section and a proximal end portion extending toward a proximal end side of the insertion section; a coupling section provided on the proximal end side of the insertion section; a rotary body which is rotatably supported in the coupling section and on which a proximal end portion of the wire is wound and held; driving force transmission means which is provided in the coupling section, includes a working shaft that is operable in a linear direction, and converts linear movement of the working shaft to rotational movement of the rotary body; a driving source unit which is detachably coupled to the coupling section and includes driving force generating means for generating a driving force for bending the bend section; and operation means which is provided in the driving source unit, includes a driving shaft that is operable in a linear direction by the driving force from the driving force generating means, and linearly moves the working shaft, when the driving source unit and the coupling section are coupled, in accordance with an operation of the driving shaft that operates in the linear direction by the driving force from the driving force generating means.

In the endoscope according to this aspect, when the coupling section on the proximal end side of the insertion section and the driving source unit are coupled, the driving shaft of the driving source unit is interlockalby engaged with the working shaft of the driving force transmission means of the coupling section. In this state, the driving shaft is linearly operated by the driving force from the driving force generating means, and the working shaft is linearly moved in accordance with the operation of the driving shaft. At this time, the linear movement of the working shaft is converted to rotational movement of the rotary body by the driving force transmission means. The wire for the bend operation of the bend section is pulled and operated by the rotational movement of the rotary body, and the bend section is bend-operated.

Preferably, the operation means includes rotary means which is rotatable by the driving force from the driving force generating means, and driving force conversion means for linearly moving the driving shaft in interlock with rotation of the rotary means.

In the above structure, the rotary means of the operation means is rotated by the driving force from the driving force generating means, and the driving shaft is linearly operated by the driving force conversion means in interlock with the rotation of the rotary means.

Preferably, the driving shaft has an abutment portion which is abutted upon an end portion of the working shaft when the driving source unit and the coupling section are coupled, and the operation means includes means for driving the working shaft in a linear operational direction by a pushing force at a time when the driving shaft is linearly moved.

In the above structure, when the driving source unit and the coupling section are coupled, the abutment portion of the driving shaft is abutted upon the end portion of the working shaft. Thereby, the working shaft is driven in a linear operational direction by a pushing force at a time when the driving shaft is linearly moved.

Preferably, the working shaft has an engagement section which is disengageably engaged with the driving shaft, and includes a removal prevention section which prevents removal of the working shaft from the driving shaft when the driving source unit and the coupling section are coupled.

In the above structure, when the driving source unit and the coupling section are coupled, the engagement section of the working shaft is disengageably engaged with the driving shaft. Thereby, removal of the working shaft from the driving shaft is prevented when the driving source unit and the coupling section are coupled.

Preferably, the rotary body includes a pinion gear, the working shaft includes a rack portion which is meshed with the pinion gear, and the driving force transmission means includes a rack-and-pinion mechanism which converts linear movement of the working shaft to rotational movement of the rotary body via a meshed portion between the rack portion and the pinion gear.

In the above structure, when the coupling section on the proximal end side of the insertion section and the driving source unit are coupled, the driving shaft is operated in the linear direction by the driving force from the driving force generating means. When the working shaft is linearly moved in accordance with the operation of the driving shaft, linear movement of the working shaft is converted to rotational movement of the rotary body via the rack-and-pinion mechanism at the meshed part between the rack portion of the working shaft and the pinion gear of the rotary body.

Thereby, it is possible to provide an endoscope wherein an attachment/detachment section between a proximal end part of an insertion section and a part that is attached/detached to/from the proximal end part can be reduced in size, and attachment/detachment is made easier between the proximal end part of the insertion section and the part that is attached/detached to/from the proximal end part.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6B is a plan view showing an arrangement state of the driving shafts and working shafts in a case where the bend section of the endoscope shown in FIG. 6A is bend-operated;

DETAILED DESCRIPTION OF THE INVENTION

Figure 1:
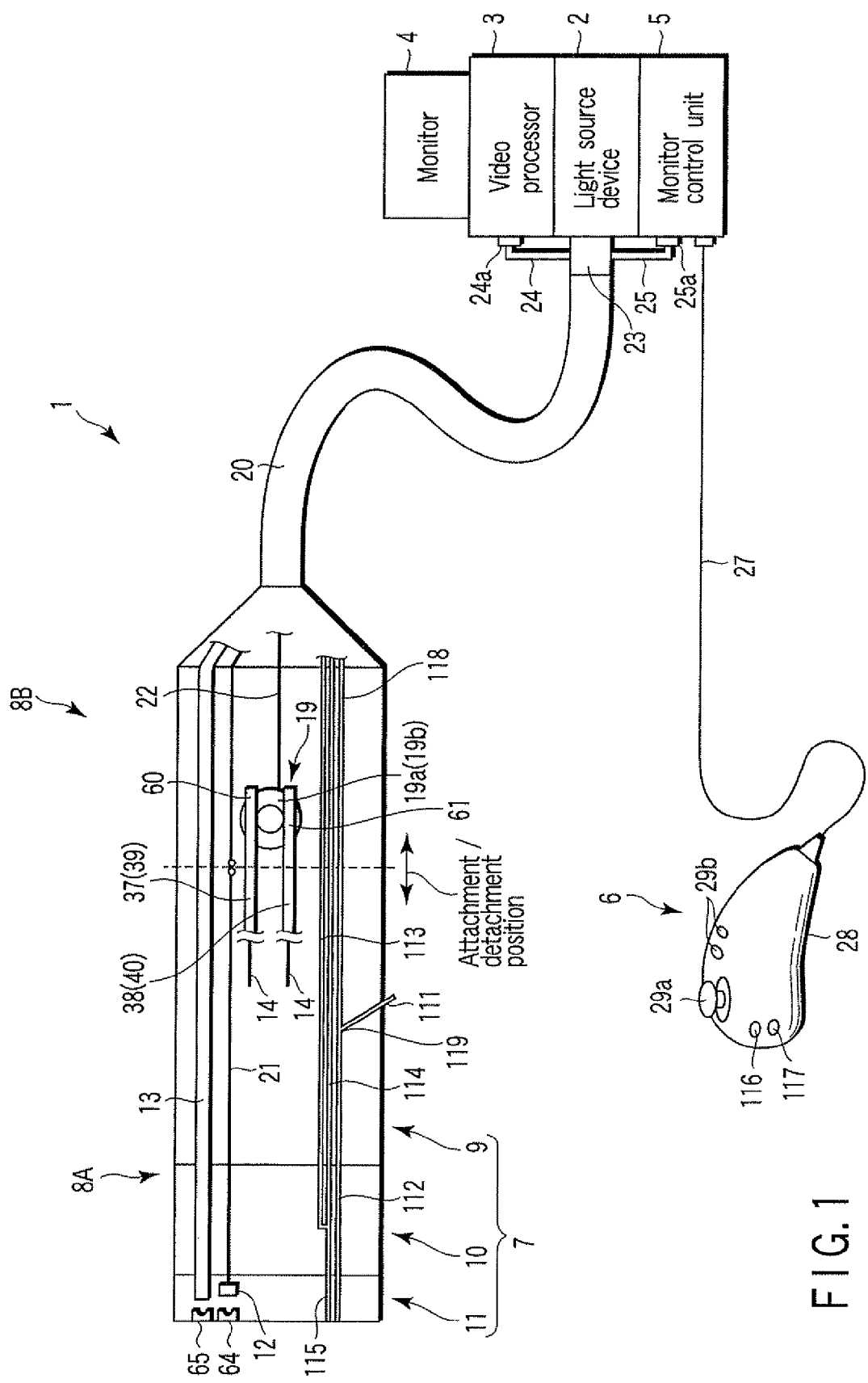
FIG. 1 schematically shows the structure of the entire system of a detachable-type endoscope according to a first embodiment of the present invention.

A first embodiment of the present invention will now be described with reference to FIG. 1 to FIG. 7B. FIG. 1 schematically shows the structure of the entire system of an endoscope according to the present embodiment. This endoscope system includes a detachable-type endoscope 1, a light source device 2, a video processor 3, a monitor 4, a motor control unit 5, and an operation unit 6 which is an input device for operating the endoscope 1.

Figure 2:
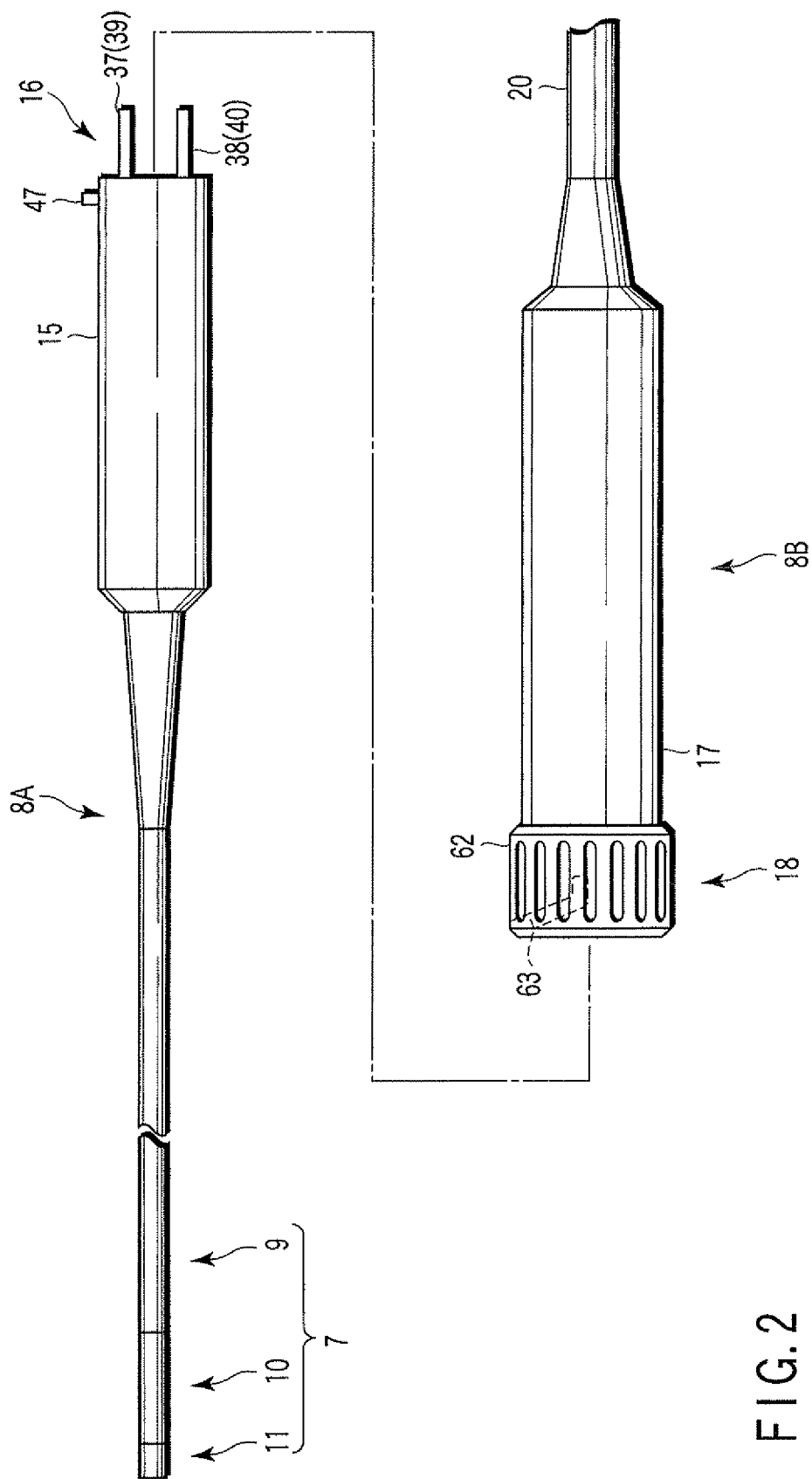
FIG. 2 is a side view showing the state in which a proximal-end-side coupling section of an insertion section of the detachable-type endoscope and a driving source unit are separated in the first embodiment.

FIG. 2 shows the detachable-type endoscope 1. The detachable-type endoscope 1 comprises a scope section 8A including an elongated insertion section 7 that is insertable in a body cavity, and a driving source unit 8B which is detachably coupled to the scope section 8A.

The insertion section 7 of the scope section 8A includes an elongated insertion tube section 9, a bend section 10 that is bendable, and a hard distal-end structure section 11. The insertion tube section 9 is formed of a hard tube section such as a metal tube, or a flexible tube section. The bend section 10 is coupled to a distal end of the insertion tube section 9. The distal-end structure section 11 is coupled to a distal end of the bend section 10.

The distal-end structure section 11 incorporates an objective lens 64, an imaging device such as a CCD 12 (see FIG. 1), an illumination lens 65, and a distal end portion of a light guide fiber 13. The imaging device photoelectrically converts an image which is focused by the objective lens 64. The light guide fiber 13 guides illumination light to the illumination lens 65.

The distal end face of the distal-end structure section 11 is provided with an opening portion of an air/water feed tube 115 (to be described later) which is built in the insertion section 7, and a distal-end opening portion of a therapeutic device insertion tube 112 (to be described later). The bend section 10 is configured such that a plurality of substantially ring-shaped bend pieces are juxtaposed in the axial direction of the insertion section 7 and the bend pieces are rotatably coupled via rotational pins such as rivets.

In addition, distal end side portions of four wires 14 for a bend operation for bend-operating the bend section 10, for example, in four directions, that is, upward, downward, leftward and rightward directions, are connected to the bend section 10. Proximal end side portions of the wires 14 are extended toward the proximal end portion of the insertion section 7.

Further, a large-diameter section (coupling section) 15 having a greater diameter than the major part of the insertion tube section 9 is provided on the proximal end side of the insertion tube section 9. A terminal end portion of the large-diameter section 15 is provided with a coupling end section 16 on the scope section 8A side, which is detachably coupled to the driving source unit 8B.

In addition, a therapeutic device insertion section 111 is provided to project from the large-diameter section 15 on the proximal end side of the scope section 8A. A therapeutic device insertion tube 112 serving also as a suction tube, a water feed tube 113 and an air feed tube 114 are provided within the scope section 8A. A distal end portion of the air feed tube 114 is connected to a distal end portion of the water feed tube 113. An air/water feed tube 115 is formed on the distal end side of the connection part between the water feed tube 113 and air feed tube 114. Besides, a proximal end portion of the therapeutic device insertion tube 112 communicates with the therapeutic device insertion section 111.

The driving source unit 8B is provided with a unit body 17 having substantially the same diameter as the large-diameter section 15 of the scope section 8A. A coupling end section 18 on the driving source unit 8B side is provided at a distal end portion of the unit body 17. The coupling end section 18 on the driving source unit 8B side is detachably coupled to the coupling end section 16 of the scope section 8A.

Driving force generating means 19 for generating a driving force for bending the bend section 10 is provided within the unit body 17. The driving force generating means 19 is provided with a driving motor 19a for an up-and-down bend operation and a driving motor 19b for a right-and-left bend operation. The driving motor 19a generates a driving force for bend-operating the bend section 10 in an up-and-down direction. The driving motor 19b generates a driving force for bend-operating the bend section 10 in a right-and-left direction.

In addition, a distal end portion of a universal cable 20 is connected to a proximal end portion of the unit body 17 of the driving source unit 8B. A CCD cable 21, a plurality of electrical cables and light guide fiber 13 are contained in the universal cable 20. The CCD cable 21 transmits a video signal from the CCD 12. The plural electrical cables include, for instance, a motor cable 22 for supplying power to the driving motors 19a, 19b of the driving force generating means 19.

A proximal end portion of the universal cable 20 is provided with a connector 23 which is detachably connected to the light source device 2. Illumination light, which is emitted from the light source device 2, is guided to the scope section 8A via the light guide fiber 13.

Further, a video cable 24, which is connected to the CCD cable 21, and a motor cable 25, which is connected to the motor cable 22, are connected to the connector 23. The video cable 24 is detachably connected to the video processor 3 via a video connector 24a. The motor cable 25 is detachably connected to the motor control unit 5 via an electrical connector 25a. The video processor 3 is connected to the monitor 4.

An observation image of the scope section 8A is captured by the CCD 12 and is converted to an electric signal. An output signal from the CCD 12 is input to the video processor 3 via the CCD cable 21 and video cable 24. The input signal is processed by the video processor 3, and an output signal from the video processor 3 is sent to the monitor 4, and the observation image of the scope section 8A is displayed on the screen of the monitor 4.

The operation unit 6 for operating the endoscope 1 is connected to the motor control unit 5 via a cable 27. The operation unit 6 includes a handpiece 28 which can be operated by one hand of the user, almost like a mouse for a personal computer. The handpiece 28 is provided with a joystick 29a for remotely bend-operating the bend section 10, an air/water feed operation button 116, a suction button 117, and other remote switches 29b.

Figure 3:
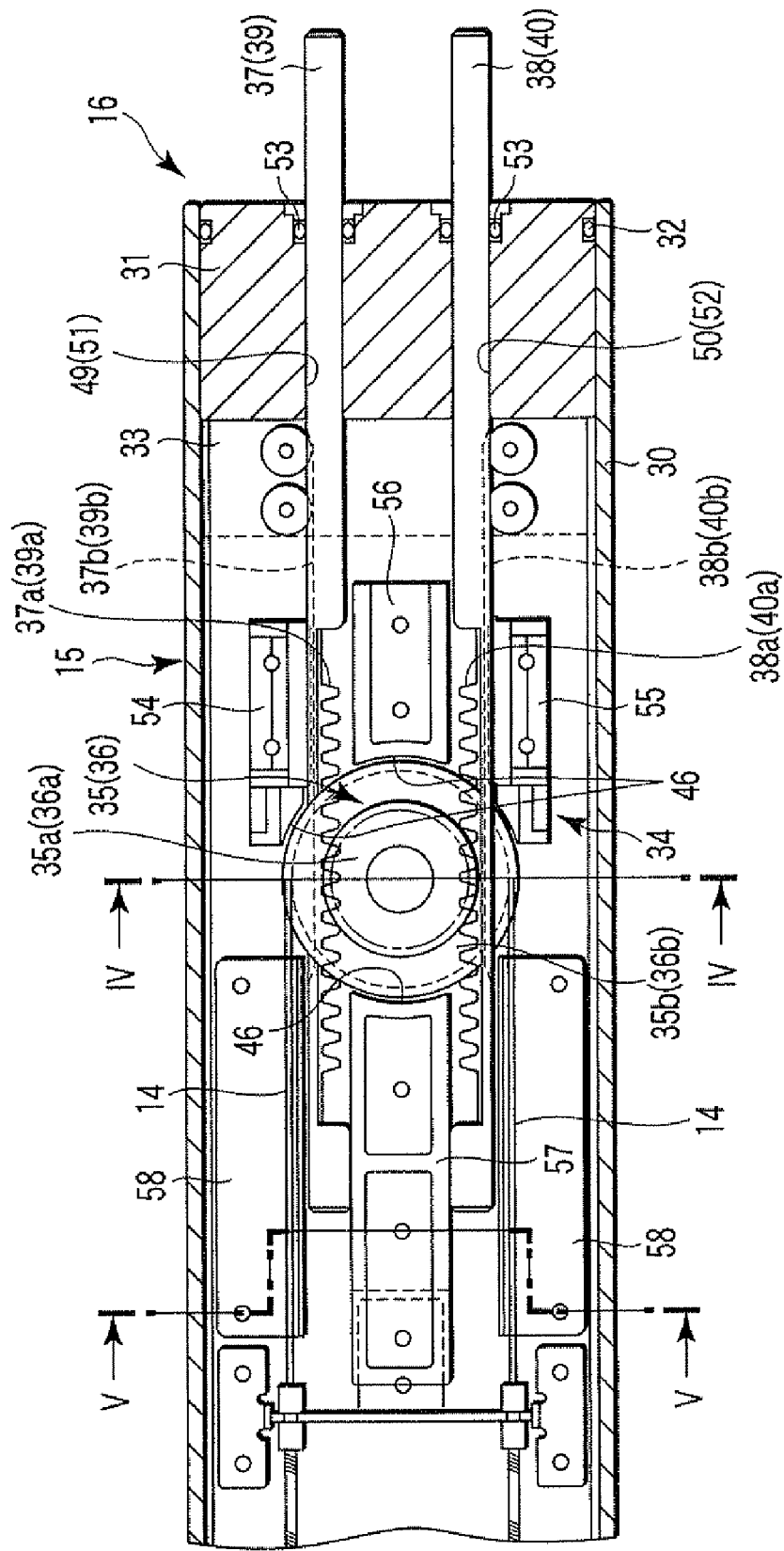
FIG. 3 is a longitudinal cross-sectional view of a main part, which shows an internal structure of the insertion section of the detachable-type endoscope according to the first embodiment.

FIG. 3 shows the internal structure of the large-diameter section 15 of the scope section 8A. The large-diameter section 15 of the scope section 8A is provided with a cylindrical cover 30, and a disc-shaped end plate 31 which is fixed in the state in which the end plate 31 closes a terminal-end-side opening portion of the cover 30. An O-ring 32 is provided between the outer peripheral surface of the end plate 31 and the inner peripheral surface of the terminal end portion of the cover 30. Water-tight sealing between the outer peripheral surface of the end plate 31 and the inner peripheral surface of the terminal end portion of the cover 30 is effected by the O-ring 32.

Figure 4:
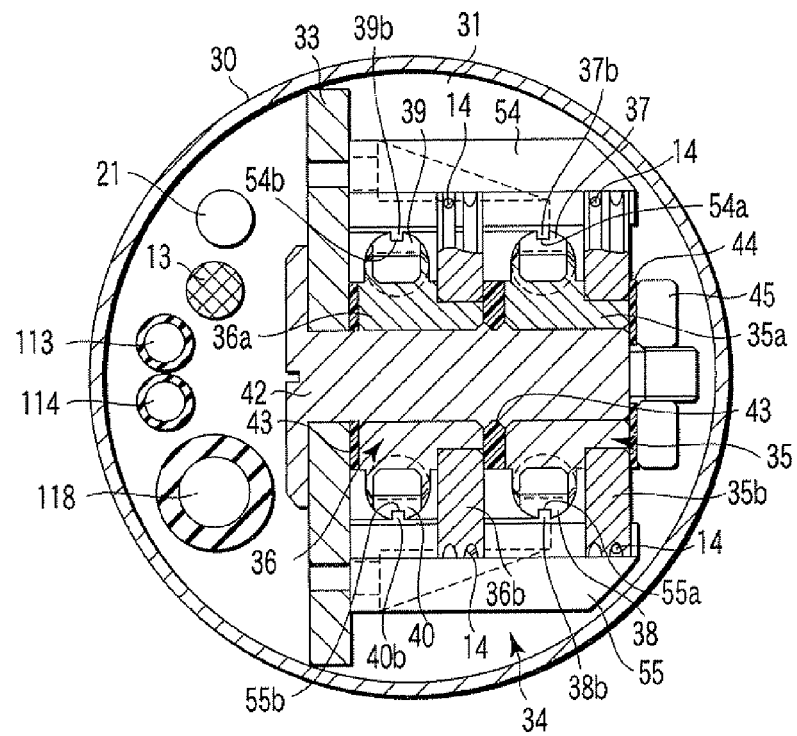
FIG. 4 is a cross-sectional view taken along line IV-IV in FIG. 3.

A base plate 33 is provided within the cover 30. As shown in FIG. 4, the base plate 33 is provided to extend over the entire length of the large-diameter section 15 in the state in which the inside of the cover 30 is substantially partitioned into two spaces by the base plate 33. One end portion of the base plate 33 is fixed to the end plate 31 by fixing screws (not shown).

In the large-diameter section 15 of the scope section 8A, driving force transmission means 34 is built in the right-side space of the base plate 33 in FIG. 4. The driving force transmission means 34 transmits a driving force for the end section 10, which is supplied from the driving source unit 8B side, as a pulling force of the wires 14 for the bend-operation. The driving force transmission means 34 includes two (first and second) rotary bodies 35 and 36 and four working shafts 37, 38, 39 and 40.

Figure 7A:
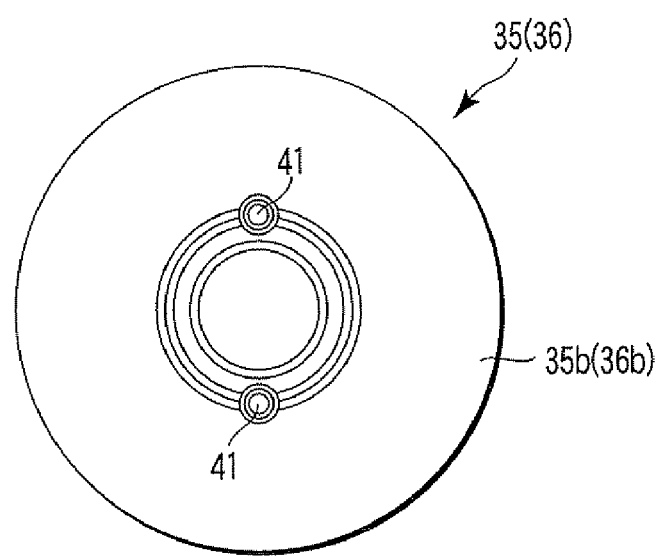
FIG. 7A is a plan view showing a coupling state of a pulley and a pinion gear of driving force transmission means which is built in a coupling section of the endoscope of the first embodiment.
Figure 7B:
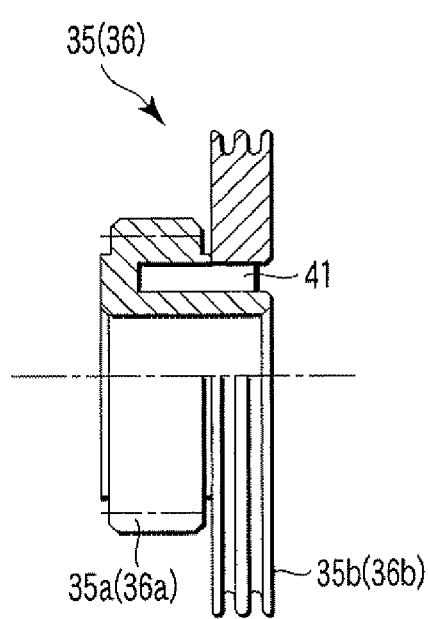
FIG. 7B is a side view showing, in cross section, an upper half of the coupling portion of the pulley and pinion gear of the driving force transmission means shown in FIG. 7A.

The first rotary body 35, or one of the rotary bodies, includes a pinion gear 35a and a pulley 35b that is fixed to the pinion gear 35a, as shown in FIG. 7A and FIG. 7B. Two pin insertion holes are formed in an engagement part between the pinion gear 35a and pulley 35b. Pins 41 are lightly fitted and fixed in the pin insertion holes. Thereby, the pinion gear 35a and pulley 35b rotate as one body.

Similarly, the second rotary body 36, or the other rotary body, includes a pinion gear 36a and a pulley 36b that is fixed to the pinion gear 36a. Two pin insertion holes are formed in an engagement part between the pinion gear 36a and pulley 36b. Pins 41 are lightly fitted and fixed in the pin insertion holes. Thereby, the pinion gear 36a and pulley 36b rotate as one body.

One pinion shaft 42 is provided to project from the base plate 33. The first rotary body 35 and second rotary body 36 are mounted on the pinion shaft 42. Resin washers 43, which are formed of, e.g. nylon or polyacetal, are disposed between the first rotary body 35 and the second rotary body 36 and between the second rotary body 36 and the base plate 33, thereby not to prevent mutual rotation.

Further, a nut 45 is engaged via a washer 44 with a distal end portion of the pinion shaft 42. Thereby, the first rotary body 35 and second rotary body 36 are journaled on the pinion shaft 42 so as be independently rotatable.

Proximal end portions of two wires 14 for, for example, an up-and-down bend operation for bend-operating the bend section 10 in an up-and-down direction are passed around and engaged with the pulley 35b of the first rotary body 35. Further, proximal end portions of two wires 14 for, for example, a right-and-left bend operation for bend-operating the bend section 10 in a right-and-left direction are passed around and engaged with the pulley 36b of the second rotary body 36.

A pair of working shafts 37 and 38 for the up-and-down bend operation are disposed in parallel and opposed to each other on both sides of the pinion gear 35a of the first rotary body 35 (i.e. upper and lower sides of the pinion gear 35a in FIG. 3 and FIG. 4). The working shafts 37 and 38 are provided with rack portions 37a and 38a which are meshed with the pinion gear 35a. Each working shaft 37, 38 is not provided with the rack portion 37a, 38a over about half the length of the working shaft 37, 38 on the proximal end portion side thereof (on the end plate 31 side), and that part of the working shaft 37, 38, which is not provided with the rack portion 37a, 38a, has a circular cross section. The distal-end-side portion of the working shaft 37, 38 is also provided with a shaft portion having a circular cross section, on which the rack portion 37a, 38a is not provided.

A pair of working shafts 39 and 40 for the right-and-left bend operation are disposed in parallel and opposed to each other on both sides of the pinion gear 36a of the second rotary body 36 (i.e. upper and lower sides of the pinion gear 36a in FIG. 3 and FIG. 4). The working shafts 39 and 40 are provided with rack portions 39a and 40a which are meshed with the pinion gear 36a. Each working shaft 39, 40 is not provided with the rack portion 39a, 40a over about half the length of the working shaft 39, 40 on the proximal end portion side thereof (on the end plate 31 side), and that part of the working shaft 39, 40, which is not provided with the rack portion 39a, 40a, has a circular cross section. The distal-end-side portion of the working shaft 39, 40 is also provided with a shaft portion having a circular cross section, on which the rack portion 39a, 40a is not provided.

A rack-and-pinion mechanism is formed which converts linear movement of the working shaft 37, 38 to rotational movement of the first rotary body 35 via an engagement portion between the rack portion 37a, 38a of the working shaft 37, 38 and the pinion gear 35a. Similarly, a rack-and-pinion mechanism is formed which converts linear movement of the working shaft 39, 40 to rotational movement of the second rotary body 36 via an engagement portion between the rack portion 39a, 40a of the working shaft 39, 40 and the pinion gear 36a.

Four passage holes 49, 50, 51 and 52 for passing the shaft portions with circular cross sections of the four working shafts 37 to 40 are formed in the end plate 31. The four working shafts 37 to 40 are passed through the passage holes 49, 50, 51 and 52 so as to be linearly movable in the axial direction of the insertion section 7. In addition, proximal-end-side shaft portions of the four working shafts 37 to 40 are held in the state in which these proximal-end-side shaft portions project outward to the outside of the large-diameter section 15 from the passage holes 49, 50, 51 and 52 of the end plate 31. Thereby, as shown in FIG. 2, the proximal-end-side shaft portions of the four working shafts 37 to 40 are held in the projecting state at the coupling end section 16 on the scope section 8A side. Besides, an engagement pin 47 (to be described later) for an attachment/detachment mechanism is provided to project from the outer peripheral surface of the proximal end portion of the large-diameter section 15 at the coupling end section 16 on the scope section 8A side.

O-rings 53 are fitted at engagement portions between the four passage holes 49, 50, 51 and 52 of the end plate 31 and the shaft portions with circular cross sections of the working shafts 37 to 40. The O-rings effect water-tight sealing of the engagement portions between the four passage holes 49, 50, 51 and 52 of the end plate 31 and the working shafts 37 to 40.

Two first guide members 54 and 55 and two second guide members 56 and 57 are fixed to the base plate 33 by screws. The two first guide members 54 and 55 guide the linear movement of the working shafts 37 to 40 from the outside of the working shafts 37 to 40. The two second guide members 56 and 57 guide the linear movement of the working shafts 37 to 40 from the inside of the working shafts 37 to 40.

The first guide member 54, which is positioned above the pinion gear 36a in FIG. 3 and FIG. 4, is provided with projections 54a and 54b for guiding, which are opposed to the working shafts 37 and 39. The projections 54a and 54b are provided to extend in the axial direction of the working shafts 37 and 39. Similarly, the first guide member 55, which is positioned below the pinion gear 36a in FIG. 3 and FIG. 4, is provided with projections 55a and 55b for guiding, which are opposed to the working shafts 38 and 40. The projections 55a and 55b are provided to extend in the axial direction of the working shafts 38 and 40.

Slit portions 38b, 38b, 39b and 40b, which extend in the axial direction, are provided in those parts of the outer peripheral surfaces of the working shafts 37 to 40, which are opposite to the rack portions 37a to 40a. The projections 54a and 54b of the first guide member 54, which is positioned above the pinion gear 36a in FIG. 3 and FIG. 4, are engaged with the slit portions 37b and 39b of the working shafts 37 and 39 so as to be slidable in the axial direction of the working shafts 37 and 39. Similarly, the projections 55a and 55b of the first guide member 55, which is positioned below the pinion gear 36a in FIG. 3 and FIG. 4, are engaged with the slit portions 38b and 40b of the working shafts 38 and 40 so as to be slidable in the axial direction of the working shafts 38 and 40.

The slit portions 37b to 40b of the working shafts 37 to 40 are not provided over the entire lengths of the working shafts 37 to 40, but are provided only on those portions opposed to the rack portions 37a to 40a.

Figure 5:
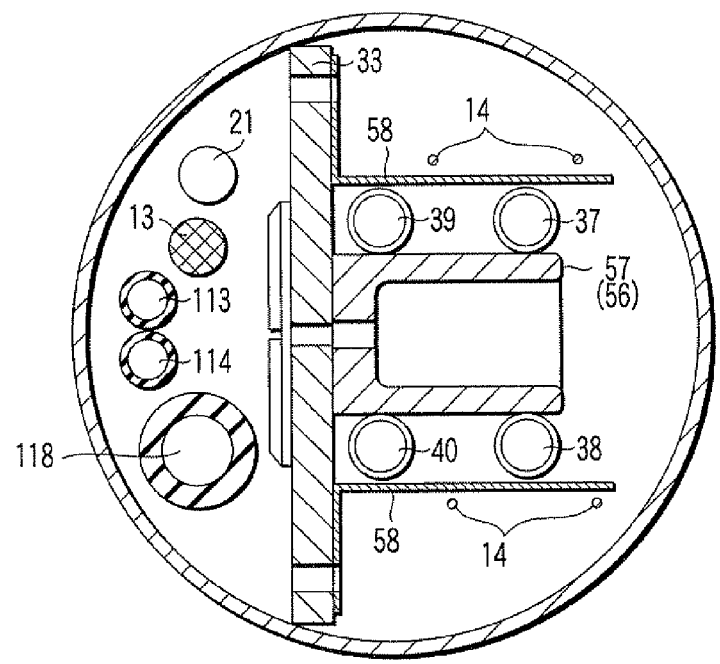
FIG. 5 is a cross-sectional view taken along line V-V in FIG. 3.

As shown in FIG. 5, the second guide members 56, 57 are disposed inside the working shafts 37 to 40 and are put in contact with the proximal-end-side shaft portions with circular cross sections of the working shafts 37 to 40 and the distal-end-side shaft portions with circular cross sections of the working shafts 37 to 40, thereby restricting the shaft portions of the working shafts 37 to 40 so as not to approach the pinion gears 35a, 35a more closely than necessary.

The two first guide members 54 and 55, which are disposed outside the working shafts 37 to 40, and the two second guide members 56 and 57, which are disposed inside the working shafts 37 to 40, restrict the positions of the working shafts 37 to 40 in directions away from the pinion gears 35a and 36a. In addition, the engagement between the slit portions 37b to 40b of the working shafts 37 to 40 and the projection portions 54a, 54b, 55a and 55b of the first guide members 54 and 55 restricts the positions of the working shafts 37 to 40 in the axial direction of the pinion shaft 42. Thereby, the operations of the working shafts 37 to 40 in the direction of linear advancement are guided.

Extension portions 46, which extend to positions close to the pulleys 35b and 36b, are formed at those parts of the first guide members 54 and 55 and second guide members 56 and 57, which are opposed to the pulley 35b of the first rotary body 35 and the pulley 36b of the second rotary body 36. The extension portions 46 of the first guide members 54 and 55 and second guide members 56 and 57 are formed to have arcuate shapes along the shapes of the pulleys 35b and 36b. Slacking of the wires 14, which are wound around the pulleys 35b and 36b, from the pulleys 35b and 36b is prevented by the extension portions 46 of the first guide members 54 and 55 and second guide members 56 and 57.

As shown in FIG. 5, substantially L-shaped interference prevention members 58, which are disposed outside the distal-end-side portions of the working shafts 37 to 40 (i.e. on the upper side of the working shafts 37 and 39 and on the lower side of the working shafts 38 and 40 in FIG. 5), are fixed to the base plate 33 by screws. The wires 14 are disposed outside the interference prevention members 58. When the bend section 10 is bend-operated, the wires 14, which are opposed to the wires 14 that are pulled for the bend-operation, are drawn to the insertion section 7 side in accordance with the bend operation. At this time, slight slacking of the wires 14 occurs inside the large-diameter section 15, but the interference prevention members 58 can prevent the slacking wires 14 from interfering with the working shafts 37 to 40 that move back and forth at the time of the bend operation.

In the large-diameter section 15 of the scope section 8A, the light guide fiber 13, CCD cable 21, water feed tube 113, air feed tube 114 and suction tube 118, which are contained in the insertion section 7 in the space on the left side of the base plate 33 in FIG. 4, are disposed.

The therapeutic device insertion tube 112 for passing a therapeutic device, which is inserted via the therapeutic device insertion section 111, is also used as a passage for sucked matter at the time of sucking. The therapeutic device insertion tube 112 is connected to the separate suction tube 118 via a branch portion 119. Sucked matter can be sucked into the suction tube 118 from the therapeutic device insertion tube 112 via the branch portion 119.

Figure 8A:
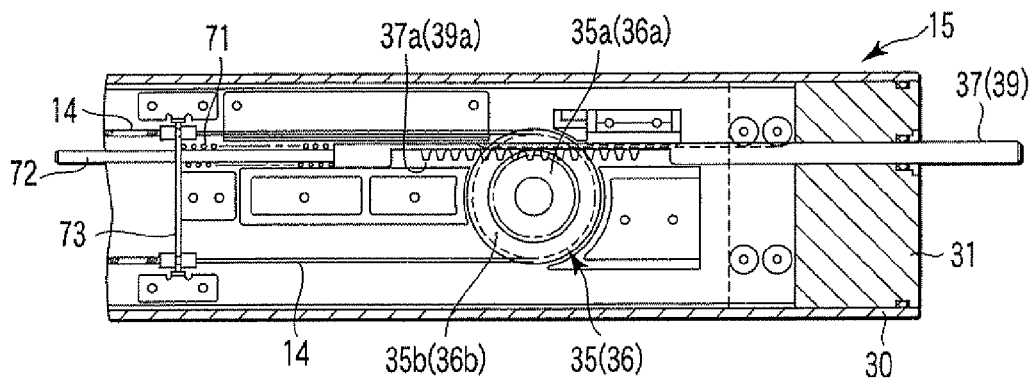
FIG. 8A is a plan view showing an arrangement state of a driving shaft and a working shaft in a case where a bend section of an endoscope according to a second embodiment of the invention is held in a non-bend state.

As shown in FIG. 8A and FIG. 5B, the driving source unit 8B is provided with the first driving motor 19a serving as the driving source for an up-and-down bend operation and the second driving motor 19b serving as the driving source for a right-and-left bend operation. In the present embodiment, bending in the four directions is exemplified. However, since the operation means for the up-and-down bend operation and the operation means for the right- and left bend operation, which are built in the driving source unit 8B, have the same structure, the structure of only the operation means for the up-and-down bend operation will be described below.

The operation means for the up-and-down bend operation includes a driving pinion 59 which is provided on the rotational shaft of the driving motor 19a, and a pair of driving shafts 60 and 61. The pair of driving shafts 60 and 61 are disposed to be opposed in parallel on both sides of the driving pinion 59 (i.e. on upper and lower sides of the driving pinion 59 in FIG. 6A, 6B). The driving shafts 60 and 61 are provided with rack portions 60a and 61a which are meshed with the driving pinion 59.

A lock ring 62 is provided on the coupling end section 18 of the driving source unit 8B. The lock ring 62 is supported on the coupling end section 18 of the driving source unit 8B so as to be rotatable about the axis thereof. The lock ring 62 is detachably coupled to the coupling end section 16 of the scope section 8A.

A cam groove 63, for instance, which is disengageably engaged with the engagement pin 47 of the coupling end section 16 of the scope section 8A, is formed in an inner peripheral surface of the lock ring 62. When the scope section 8A and the driving source unit 8B are to be coupled, the coupling end section 16 of the scope section 8A and the coupling end section 18 of the driving source unit 8B are abutted upon each other. At this time, the engagement pin 47 on the scope section 8A side is inserted in and engaged with the cam groove 63 of the driving source unit 8B. In this state, the lock ring 62 is rotated over a desired rotational angle. Thereby, the engagement pin 47 is moved to the lock position at the terminal end of the cam groove 63, and the scope section 8A and the driving source unit 8B are locked in the coupled state.

In addition, when the scope section 8A and the driving source unit 8B are to be coupled, the end faces of the proximal-end-side portions of the paired working shafts 37 and 38 for the up-and-down bend operation on the scope section 8A side are abutted upon the end faces of the distal-end-side portions of the driving shafts 60 and 61 for the up-and-down bend operation of the driving source unit 8B. At the same time, the end faces of the proximal-end-side portions of the paired working shafts 39 and 40 for the right-and-left bend operation are set to be abutted upon the end faces of the distal-end-side portions of the driving shafts 60 and 61 for the right-and-left bend operation of the driving source unit 8B. In this state, the working shafts 37 and 38 advance and retreat in interlock with the advancement/retreat of the driving shafts 60 and 61 for the up-and-down bend operation of the driving source unit 8B, and thus the bend section 10 is bend-operated in the up-and-down direction. In addition, the working shafts 39 and 40 advance and retreat in interlock with the advancement/retreat of the driving shafts 60 and 61 for the right-and-left bend operation of the driving source unit BB, and thus the bend section 10 is bend-operated in the right-and-left direction.

Furthermore, connection parts of the light guide fiber 13, CCD cable 21, water feed tube 113, air feed tube 114 and suction tube 118, which are contained in the insertion section 7, are provided at the coupling section between the coupling end section 18 of the driving source unit 8B and the coupling end section 16 of the scope section 8A. When the scope section 8A and the driving source unit 8B are to be coupled, the connection parts of the light guide fiber 13, CCD cable 21, water feed tube 113, air feed tube 114 and suction tube 118 on the scope section 8A side are detachably connected to the connection parts of the light guide fiber 13, CCD cable 21, water feed tube 113, air feed tube 114 and suction tube 118 on the driving source unit 8B side.

Next, the operation of the above-described structure is described. When the detachable-type endoscope 1 of this embodiment is used, the scope section 8A and the driving source unit 8B are coupled and used. At the time of the work of coupling the scope section 8A and the driving source unit 8B, the coupling end section 16 of the scope section 8A and the coupling end section 18 of the driving source unit 8B are abutted upon each other. At this time, the engagement pin 47 on the scope section 8A side is inserted in and engaged with the cam groove 63 of the driving source unit 8B. In this state, the lock ring 62 is rotated over a desired rotational angle. Thereby, the engagement pin 47 is moved to the lock position at the terminal end of the cam groove 63, and the scope section 8A and the driving source unit 8B are locked in the coupled state.

In addition, when the scope section 8A and the driving source unit 8B are to be coupled, the end faces of the proximal-end-side portions of the paired working shafts 37 and 38 for the up-and-down bend operation on the scope section 8A side are abutted upon the end faces of the distal-end-side portions of the driving shafts 60 and 61 for the up-and-down bend operation of the driving source unit 8B. At the same time, the end faces of the proximal-end-side portions of the paired working shafts 39 and 40 for the right-and-left bend operation are set to be abutted upon the end faces of the distal-end-side portions of the driving shafts 60 and 61 for the right-and-left bend operation of the driving source unit 8B.

Figure 6A:
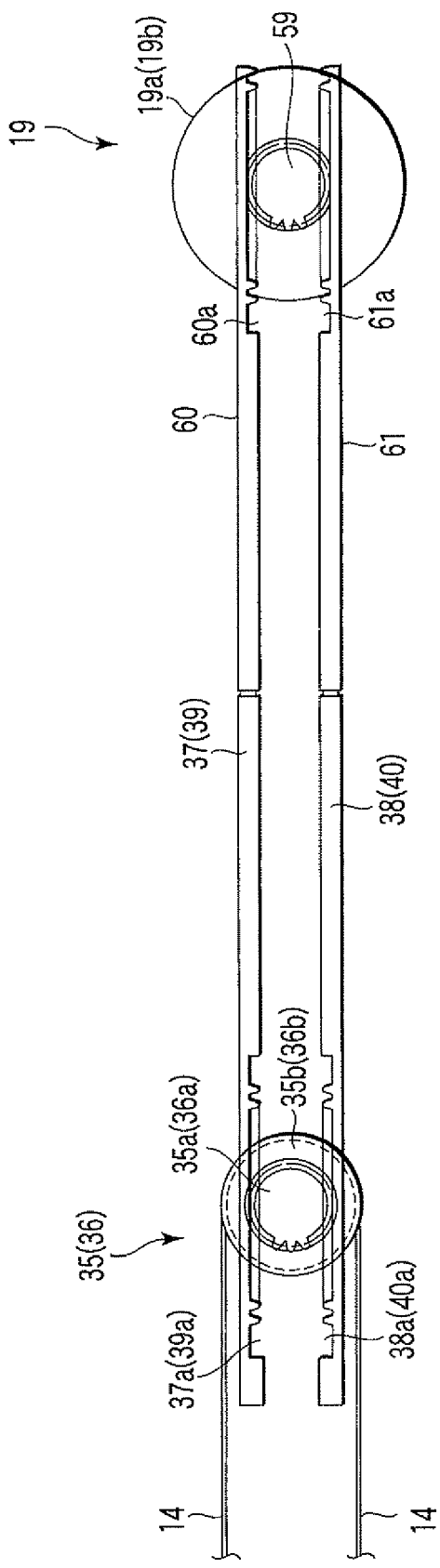
FIG. 6A is a plan view showing an arrangement state of driving shafts and working shafts in a case where the bend section of the endoscope of the first embodiment is held in a non-bend state.

As shown in FIG. 6A, in the initial state of coupling between the scope section 8A and the driving source unit 8B, the distal-end-side portions of the driving shafts 60 and 61 for the up-and-down bend operation of the driving source unit 8B and the distal-end-side portions of the driving shafts 60 and 61 for the right-and-left bend operation of the driving source unit 8B are held at substantially the same fixed position. At this time, the bend section 10 of the scope section 8A is held in a substantially straight linear shape, without bend.

Further, the connection parts of the light guide fiber 13, CCD cable 21, water feed tube 113, air feed tube 114 and suction tube 118 on the scope section 8A side are detachably connected to the connection parts of the light guide fiber 13, CCD cable 21, water feed tube 113, air feed tube 114 and suction tube 118 on the driving source unit 8B side.

The endoscope 1 is used in the state in which the coupling work between the scope section 8A and the driving source unit 8B is completed and the scope section 8A and the driving source unit 8B are assembled. When the endoscope 1 is used, the movement of the endoscope 1 is controlled by operating the handpiece 28 of the operation unit 6. Specifically, the bend section 10 is remotely bend-operated by operating the joystick 29a of the handpiece 28. Furthermore, the endoscope operations corresponding to the functions of the remote switches 29b are performed by operating the remote switches 29b.

When the bend section 10 is bend-operated, the joystick 29a of the handpiece 28 is operated and turned in a desired operation direction. A signal, which occurs in accordance with the turning operation of the joystick 29a, is input to the motor control unit 5. In addition, when the joystick 29a is turned and operated, a control signal corresponding to the turning operation of the joystick 29a is output from the motor control unit 5, and at least one of the driving motor 19a for the up-and-down bend operation and the driving motor 19b for the right-and-left bend operation, which are provided in the driving source unit 8B, is driven.

In the case where the driving motor 19a for the up-and-down bend operation is driven, the driving pinion 59 of the driving motor 19a is rotated. When the driving pinion 59 is rotated, the paired driving shafts 60 and 61 are advanced/retreated in the axial direction via the meshed portion between the driving pinion 59 and the rack portions 60a and 61a. At this time, the paired driving shafts 60 and 61 are advanced/retreated in opposite directions by the same distance. For example, one driving shaft 60 is advanced by a predetermined distance toward the scope section 8A, and the other driving shaft 61 is retreated in a direction away from the scope section 8A by a distance that is equal to the distance of the advancement of the driving shaft 60.

In addition, the end faces of the proximal-end-side portions of the paired working shafts 37 and 38 for the up-and-down bend operation on the scope section 8A side are abutted upon the end faces of the distal-end-side portions of the driving shafts 60 and 61 for the up-and-down bend operation of the driving source unit 8B. Thus, the paired working shafts 37 and 38 for the up-and-down bend operation on the scope section 8A side advance and retreat in interlock with the advancement/retreat operation of the driving shafts 60 and 61 for the up-and-down bend operation of the driving source unit 8B.

At this time, for example, as shown in FIG. 6B, one working shaft 38 is pushed forward by the driving shaft 61 that advances toward the scope section 8A, and the working shaft 38 advances toward the distal end of the scope section 8A. In interlock with the advancement operation of the working shaft 38, the pinion gear 35a of the first rotary body 35 rotates clockwise. When the pinion gear 35a is rotated, the pulley 35b also rotates together with the pinion gear 35a. Accordingly, with the clockwise rotational operation of the pulley 35b, the upper-side wire 14 that is wound around the pulley 35b, as shown in FIG. 6B, is pulled toward the driving source unit 8B. The up-and-down bend operation of the bend section 10 is performed in accordance with the pulling operation of this wire 14.

In addition, when the pinion gear 35a is rotated, the working shaft 37, which is opposed to the working shaft 38, is retreated toward the driving source unit 8B by the distance that is equal to the distance of advancement of the working shaft 38 in interlock with the rotational operation of the pinion gear 35a. At this time, the retreat operation of the working shaft 37 and the retreat operation of the driving shaft 61 are synchronized and performed at the same time.

When the driving motor 19b for the right-and-left bend operation is driven, the paired driving shafts 60 and 61 for the right-and-left bend operation are advanced/retreated in the axial direction by substantially the same operation. Moreover, the paired working shafts 39 and 40 for the right-and-left bend operation on the scope section 8A side advance and retreat in interlock with the advancement/retreat of the driving shafts 60 and 61. At this time, in interlock with the advancement/retreat operation of the working shafts 39 and 40, the pinion gear 36a of the second rotary body 36 rotates, and the pulley 36b also rotates together with the pinion gear 36a. Accordingly, with the rotational operation of the pulley 36b, the wire 14 that is wound around the pulley 36b is pulled toward the driving source unit 8B. The right-and-left bend operation of the bend section 10 is performed in accordance with the pulling operation of this wire 14.

By the combination of the up-and-down bend operation and the right-and-left bend operation of the bend section 10, the distal-end structure section 11 of the insertion section 7 of the scope section 8A can be bent in a desired direction.

The following advantageous effects can be obtained by the above-described structure. Specifically, according to the present embodiment, there is provided the detachable-type endoscope 1 in which the scope section 8A having the elongated insertion section 7, which is insertable in the body cavity, and the driving source unit BB are detachably coupled. The driving source unit BB is provided with two driving motors 19a and 19b for the up-and-down bend operation and right-and-left bend operation, and a pair of driving shafts 60 and 61 which are advanced/retreated in the axial direction in opposite directions by the same distance by the driving motors 19a and 19b. Furthermore, the driving force transmission means 34, which transmits a driving force for the end section 10, which is supplied from the driving source unit 8B side, as a pulling force of the wires 14 for the bend-operation, is built in the large-diameter section 15 at the proximal end portion of the scope section 8A. The driving force transmission means 34 includes two (first and second) rotary bodies 35 and 36 and four working shafts 37, 38, 39 and 40. The first rotary body 35 includes a pinion gear 35a and a pulley 35b, which rotate as one body. The second rotary body 36 includes a pinion gear 36a and a pulley 36b, which rotate as one body. The first rotary body 35 and second rotary body 36 are journaled on the pinion shaft 42 so as be independently rotatable. Proximal end portions of two wires 14 for the up-and-down bend operation for bend-operating the bend section 10 in the up-and-down direction are passed around and engaged with the pulley 35b of the first rotary body 35, and proximal end portions of two wires 14 for the right-and-left bend operation for bend-operating the bend section 10 in the right-and-left direction are passed around and engaged with the pulley 36b of the second rotary body 36. A pair of working shafts 37 and 38 for the up-and-down bend operation are disposed in parallel and opposed to each other on both sides of the pinion gear 35a of the first rotary body 35. The working shafts 37 and 38 are provided with rack portions 37a and 38a which are meshed with the pinion gear 35a. Thereby, a rack-and-pinion mechanism is formed which converts linear movement of the working shaft 37, 38 to rotational movement of the first rotary body 35 via a meshed portion between the rack portion 37a, 38a of the working shaft 37, 38 and the pinion gear 35a. Similarly, a pair of working shafts 39 and 40 for the right-and-left bend operation are disposed in parallel and opposed to each other on both sides of the pinion gear 36a of the second rotary body 36. The working shafts 39 and 40 are provided with rack portions 39a and 40a which are meshed with the pinion gear 36a. Thereby, a rack-and-pinion mechanism is formed which converts linear movement of the working shaft 39, 40 to rotational movement of the second rotary body 36 via a meshed portion between the rack portion 39a, 40a of the working shaft 39, 40 and the pinion gear 36a.

In the present embodiment, when the scope section 8A and the driving source unit 8B are to be coupled, the end faces of the proximal-end-side portions of the paired working shafts 37 and 38 for the up-and-down bend operation on the scope section 8A side are abutted upon the end faces of the distal-end-side portions of the driving shafts 60 and 61 for the up-and-down bend operation of the driving source unit 8B. At the same time, the end faces of the proximal-end-side portions of the paired working shafts 39 and 40 for the right-and-left bend operation are set to be abutted upon the end faces of the distal-end-side portions of the driving shafts 60 and 61 for the right-and-left bend operation of the driving source unit 8B. In this state, the working shafts 37 and 38 advance and retreat in interlock with the advancement/retreat of the driving shafts 60 and 61 for the up-and-down bend operation of the driving source unit 8B, and thus the bend section 10 is bend-operated in the up-and-down direction. In addition, the working shafts 39 and 40 advance and retreat in interlock with the advancement/retreat of the driving shafts 60 and 61 for the right-and-left bend operation of the driving source unit 8B, and thus the bend section 10 is bend-operated in the right-and-left direction. As a result, in the present embodiment, the rack-and-pinion mechanism, which converts linear movement of the working shaft 37, 38 to rotational movement of the first rotary body 35 via a meshed portion between the rack portion 37a, 38a of the working shaft 37, 38 and the pinion gear 35a, and the rack-and-pinion mechanism, which converts linear movement of the working shaft 39, 40 to rotational movement of the second rotary body 36 via a meshed portion between the rack portion 39a, 40a of the working shaft 39, 40 and the pinion gear 36a, are assembled in the large-diameter section 15 at the proximal end portion of the scope section 8A. Thereby, compared to the prior art, the coupling section between the scope section 8A and the driving source unit 8B of the endoscope 1 can be reduced in size, and the coupling section between the scope section 8A and the driving source unit 8B can easily be detached/attached.

Figure 8B:
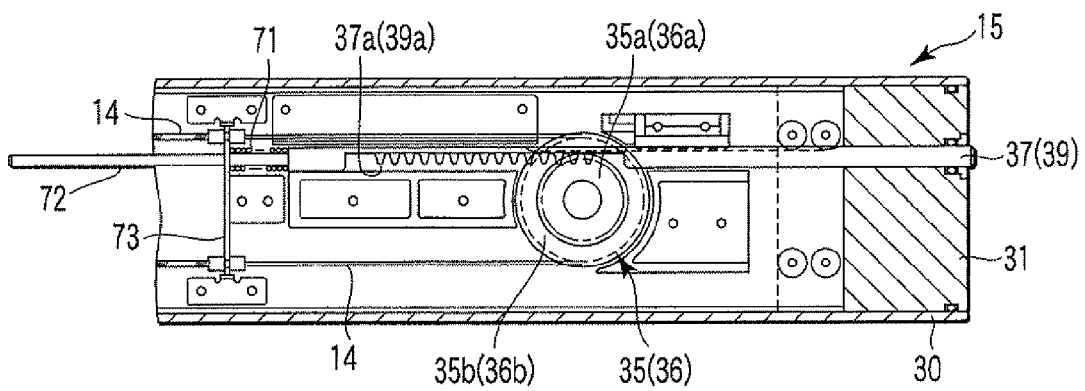
FIG. 8B is a plan view showing an arrangement state of the driving shaft and working shaft in a case where the bend section shown in FIG. 8A is bend-operated in one direction.
Figure 8C:
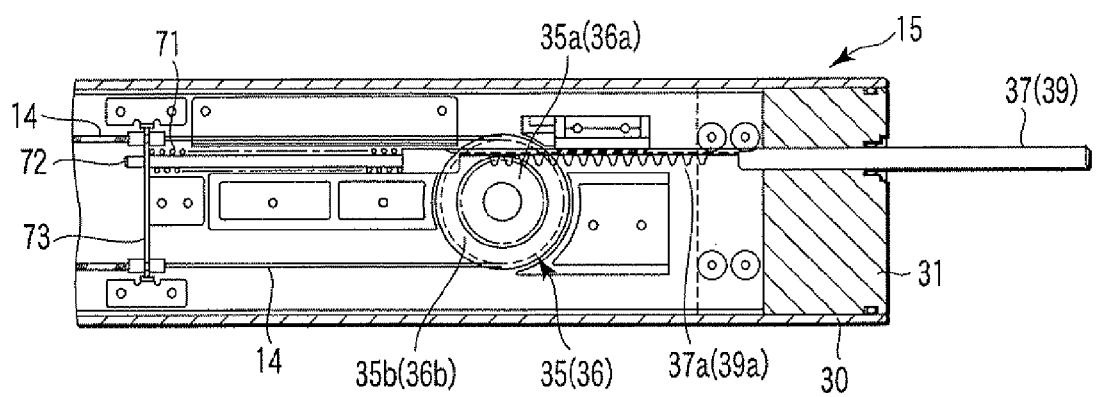
FIG. 8C is a plan view showing an arrangement state of the driving shaft and working shaft in a case where the bend section shown in FIG. 8A is bend-operated in the other direction.

FIG. 8A to FIG. 8C show a second embodiment of the present invention. In this embodiment, the structure of the driving force transmission means 34, which is built in the large-diameter section 15 of the scope section 8A of the detachable-type endoscope 1 according to the first embodiment (see FIG. 1 to FIG. 7B), is altered as described below. The other structural parts are the same as those of the detachable-type endoscope 1 according to the first embodiment. The parts common to those of the detachable-type endoscope 1 according to the first embodiment are denoted by like reference numerals, and a description thereof is omitted.

Specifically, in the first embodiment, the working shafts 37, 38, 39 and 40 are disposed on both sides of the pinion gears 35a and 36a of the two (first and second) rotary bodies 35 and 36. When the bend section 10 is to be bend-operated, the working shafts 37, 38, 39 and 40 on both sides of the pinion gears 35a and 36a are moved in opposite directions in interlock with the rotational operations of the pinion gears 35a and 36a. By contrast, in the present embodiment, the working shafts 37 and 39 are provided only on one side of the first and second rotary bodies 35 and 36.

In addition, in the present embodiment, a coil spring 71 is provided for constantly urging the working shaft 37, 39 toward the driving source unit 8B. A small-diameter portion 72 is provided on a distal-end side of each working shaft 37, 39. Besides, a coil sheath receiver 73 is provided to project from the base plate 33 on the bend section 10 side of the first and second rotary bodies 35 and 36. Passage holes for passing the small-diameter portions 72 of the working shafts 37 and 39 are formed in the coil sheath receiver 73.

The coil spring 71 is provided in the state in which the coil spring 71 is fitted over the periphery of the small-diameter portion 72 of each working body 37, 39. One end portion of the coil spring 71 is fixed in the state in which this end portion is in contact with the coil sheath receiver 73. The other end portion of the coil spring 71 is fixed in the state in which this end portion is in contact with a stepped portion between the small-diameter portion 72 of the working shaft 37, 39 and the body of the working shaft 37, 39. Thereby, the working shaft 37, 39 is constantly urged toward the driving source unit 8B by the spring force of the coil spring 71.

Next, the operation of the above-described structure is described. In the detachable-type endoscope 1 of the present embodiment, when the driving source unit 8B and the scope section 8A are to be coupled, each working shaft 37, 39 is held in a neutral position shown in FIG. 8A in the case of the normal state in which the bend section 10 is held in a non-bent straight state.

At the time of bend-operating the bend section 10, in the case where the working shaft 37, 39 is pushed toward the distal end portion of the scope section 8A against the spring force of the coil spring 71, as shown in FIG. 8B, by the driving shaft 60 (see FIG. 6A and FIG. 6B) that is in contact with the end face of the working shaft 37, 39 on the driving source unit 8B side, the pinion gear 35a, 36a and the pulley 35b, 36b rotate counterclockwise in FIG. 8B in accordance with the movement of the working shaft 37, 39. Thereby, the wire 14, which is positioned on the lower side in FIG. 8B, is pulled and the bend section 10 is bent, for example, upward (or leftward).

When the bend section 10 is to be bend-operated, the working shaft 37, 39 is urged by the spring force of the coil spring 71 so as to be constantly in contact with the end face of the distal end portion of the driving shaft 60. Thus, in the case where the working shaft 37, 39 has moved toward the driving source unit 8B side, as shown in FIG. 5C, the pinion gear 35a, 36a and the pulley 35b, 36b rotate clockwise in FIG. 8C in accordance with the movement of the working shaft 37, 39. Thereby, the wire 14, which is positioned on the upper side in FIG. 5C, is pulled and the bend section 10 is bent, for example, downward (or rightward).

The following advantageous effects can be obtained by the above-described structure. Specifically, in the present embodiment, the structure of the driving force transmission means 34, which is provided in the large-diameter section 15 of the scope section 8A of the detachable-type endoscope 1 according to the first embodiment, is altered such that the working shafts 37 and 39 are provided only on one side of the first and second rotary bodies 35 and 36 and that the coil spring 71 is provided for constantly urging the working shaft 37, 39 toward the driving source unit BB. In this case, if the working shafts 37 and 39 are merely provided only on one side of the first and second rotary bodies 35 and 36, the working shaft 37, 39 cannot be moved toward the driving source unit BB in accordance with the movement of the driving shaft 60 in the case where the driving shaft 60 moves toward the driving source unit 8B. To cope with this, the working shaft 37, 39 is urged by the coil spring 71 so as to be constantly in contact with the end face of the distal end portion of the driving shaft 60. Thereby, when the driving shaft 60 has moved toward the driving source unit 8B, the working shaft 37, 39 can be moved toward the driving source unit 8B in accordance with the movement of the driving shaft 60. As a result, in the present embodiment, the pinion gear 35a (or 36a) and the pulley 35b (or 36b) can be rotated by the single working shaft 37 (or 39) having the rack gear 37a (or 39a) which is meshed with the pinion gear 35a (or 36a) that is formed integral with the pulley 35b (or 36b) for winding up the wire 14, and the bend operation can be performed by winding up the wire 14. Therefore, it is possible to provide the scope section 8B of the detachable-type endoscope 1 in which the number of parts is smaller, the structure is simpler and the cost is lower than in the structure of the first embodiment (see FIG. 3).

Figure 9A:
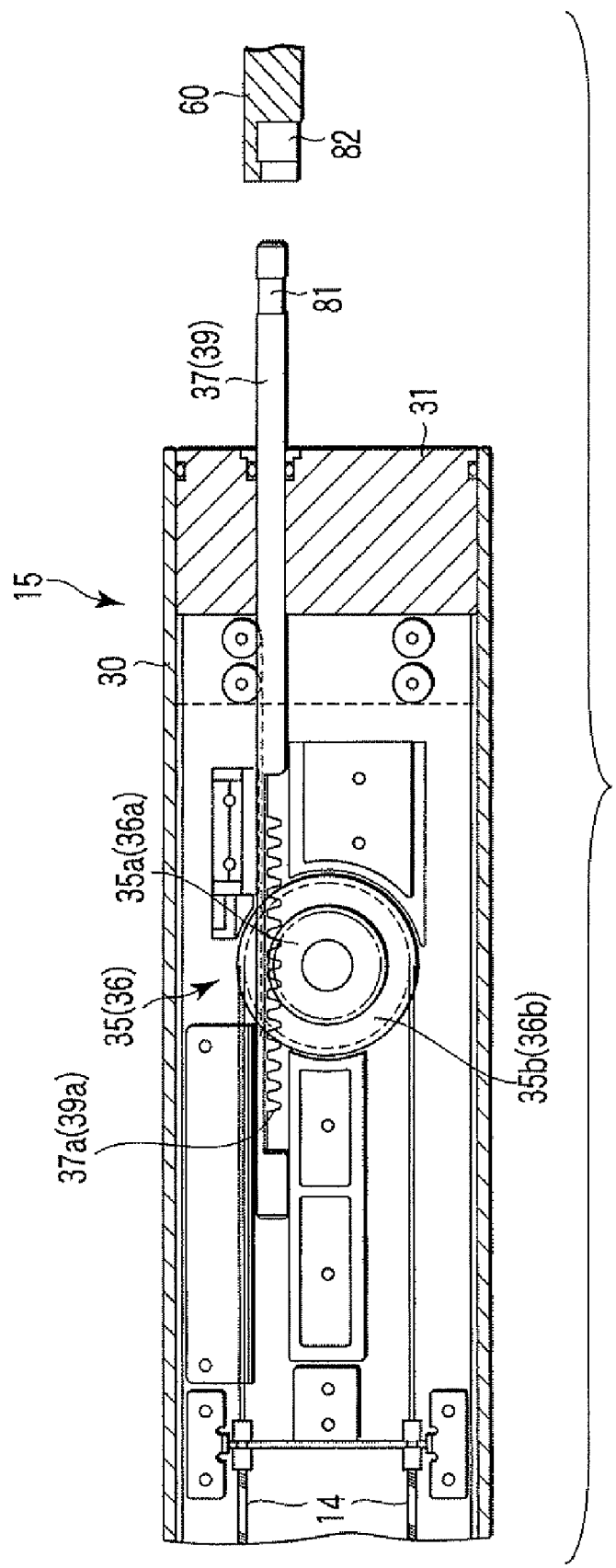
FIG. 9A is a longitudinal cross-sectional view of a main part, which shows a state in which an engagement section between a driving shaft and a working shaft of an endoscope according to a third embodiment of the invention is separated.
Figure 9B:
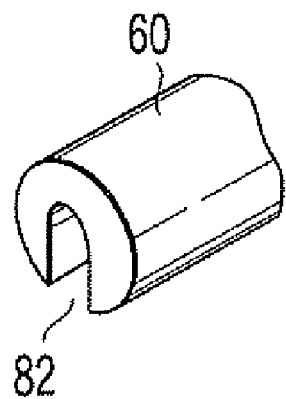
FIG. 9B is a perspective view showing a notch portion of the driving shaft shown in FIG. 9A.
Figure 9C:
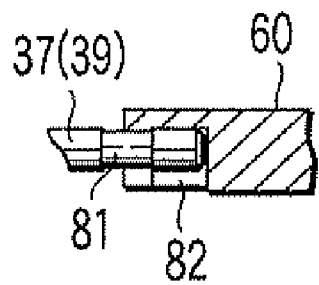
FIG. 9C is a longitudinal cross-sectional view of a main part, which shows a state in which the engagement section between the driving shaft and working shaft shown in FIG. 9A is engaged.

FIG. 9A to FIG. 9C show a third embodiment of the present invention. In this embodiment, the structure of the driving force transmission means 34, which is built in the large-diameter section 15 of the scope section 8A of the detachable-type endoscope 1 according to the first embodiment (see FIG. 1 to FIG. 7B), is altered as described below. The other structural parts are the same as those of the detachable-type endoscope 1 according to the first embodiment. The parts common to those of the detachable-type endoscope 1 according to the first embodiment are denoted by like reference numerals, and a description thereof is omitted.

Specifically, in this embodiment, like the second embodiment (see FIG. 8A to FIG. 8C), the working shafts 37 and 39 are provided only on one side of the first and second rotary bodies 35 and 36. In addition, a stepped portion (engaging portion) 81, which is formed of an annular recess portion, is provided at a shaft end portion of the working shaft 37, 39 on the driving source unit 8B side. Furthermore, as shown in FIG. 9B, the driving shaft 60 on the driving source unit 8B side is provided with a stepped notch portion 82 which corresponds to the stepped portion 81 of the working shaft 37, 39. When the driving source unit 8B and the scope unit 8R are coupled, the stepped portion 81 of the working shaft 37, 39 is detachably engaged with the notch portion 82 of the driving shaft 60, as shown in FIG. 9C. Thereby, a removal prevention section is formed which prevents removal of the working shaft 37, 39 from the driving shaft 60.

Next, the operation of the above-described structure is described. In the detachable-type endoscope 1 of this embodiment, prior to the coupling between the driving source unit 8B and the scope section 8A, as shown in FIG. 9A, the stepped portion 81 of the working shaft 37, 39 and the notch portion 82 of the driving shaft 60 are held in the separated state.

When the driving source unit 8B and the scope section 8A are to be coupled, the stepped portion 81 of the working shaft 37, 39 is detachably engaged with the notch portion 82 of the driving shaft 60, as shown in FIG. 9C. At this time, hook-like engagement is effected between the stepped portion 81 of the working shaft 37, 39 and the notch portion 82 of the driving shaft 60. Therefore, in the state in which the stepped portion 81 of the working shaft 37, 39 and the notch portion 82 of the driving shaft 60 are engaged, the engagement therebetween is not released even if the working shaft 37, 39 and the driving shaft 60 are moved in the axial direction.

According to this structure, when the driving shaft 60 moves toward the scope section 8A, an inner end part of the notch portion 82 of the driving shaft 60 abuts on the end portion of the working shaft 37, 39 on the driving source unit BB side, and moves the working shaft 37, 39 toward the distal end of the scope section 8A. In accordance with the movement of the working shaft 37, 39 at this time, the pinion gear 35a, 36a and the pulley 35b, 36b rotate counterclockwise in FIG. 9A. Thereby, the wire 14, which is positioned on the lower side in FIG. 9A, is pulled and the bend section 10 is bent, for example, upward (or leftward).

When the driving shaft 60 moves toward the driving source unit 8B, the end face of the notch portion 82 of the driving shaft 60, which is engaged with the stepped portion 81 of the working shaft 37, 39, pulls the stepped portion 81 of the working shaft 37, 39, and moves the working shaft 37, 39 toward the driving source unit 8B. In accordance with the movement of the working shaft 37, 39 at this time, the pinion gear 35a, 36a and the pulley 35b, 36b rotate clockwise in FIG. 9A. Thereby, the wire 14, which is positioned on the upper side in FIG. 9A, is pulled and the bend section 10 is bent, for example, downward (or rightward).

The following advantageous effects can be obtained by the above-described structure. Specifically, in the present embodiment, the structure of the driving force transmission means 34, which is provided in the large-diameter section 15 of the scope section 8A of the detachable-type endoscope 1 according to the first embodiment, is altered such that the working shafts 37 and 39 are provided only on one side of the first and second rotary bodies 35 and 36, the stepped portion 81 is provided at the shaft end portion of the working shaft 37, 39 on the driving source unit 8B side, and the driving shaft 60 on the driving source unit 8B side is provided with the stepped notch portion 82. Thus, when the driving source unit 8B and the scope unit 8A are coupled, the stepped portion 81 of the working shaft 37, 39 is detachably engaged with the notch portion 82 of the driving shaft 60, as shown in FIG. 9C. Thereby, the removal prevention section is formed which prevents removal of the working shaft 37, 39 from the driving shaft 60. Therefore, it is possible to provide the scope section 8B of the detachable-type endoscope 1 in which the number of parts is smaller, the structure is simpler and the cost is lower than in the structure of the first embodiment (see FIG. 3).

Figure 10:
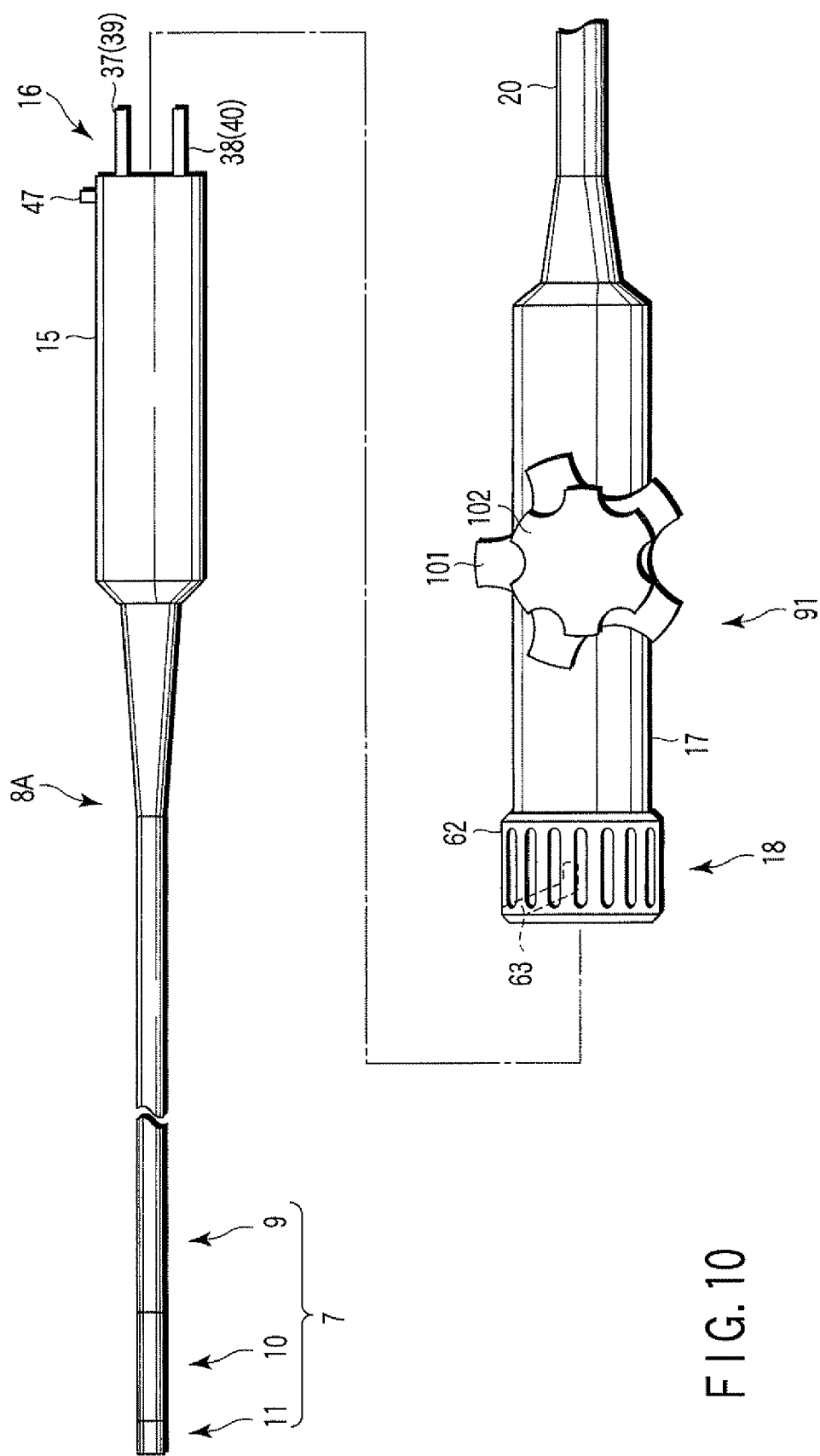
FIG. 10 is a side view showing the state in which a proximal-end-side coupling section of an insertion section of a detachable-type endoscope according to a fourth embodiment of the invention and a driving source unit are separated.

FIG. 10 shows a fourth embodiment of the present invention. In this embodiment, the motor-type driving force generating means 19, which is provided in the driving source unit 8B of the detachable-type endoscope 1 according to the first embodiment (see FIG. 1 to FIG. 7B), is replaced with manual-type driving force generating means 91. The other structural parts are the same as those of the detachable-type endoscope 1 according to the first embodiment. The parts common to those of the detachable-type endoscope 1 according to the first embodiment are denoted by like reference numerals, and a description thereof is omitted.

Specifically, in the manual-type driving force generating means 91 according to the present embodiment, an operation knob 101 for the up-and-down bend operation and an operation knob 102 for the right-and-left bend operation are provided on a side surface of the driving source unit 8B. The operation knobs 101 and 102 are independently rotatably journaled on the same axis.

The driving source unit 8B contains a bend driving mechanism (not shown) which converts the operation force of the operation knob 101, 102 to a linear advancement/retreat operation of the driving shaft 60, 61 in the axial direction.

When the scope section 8A and the driving source unit 8B are coupled, the paired driving shafts 60 and 61 are advanced/retreated in opposite directions by the same distance in accordance with the rotational operation of the operation knob 101, 102 on the scope section 8A side.

The end faces of the proximal-end-side portions of the paired working shafts 37 and 38 for the up-and-down bend operation on the scope section 8A side are abutted upon the end faces of the distal-end-side portions of the driving shafts 60 and 61 for the up-and-down bend operation of the driving source unit BB. Thus, the paired working shafts 37 and 38 for the up-and-down bend operation on the scope section 8A side advance and retreat in interlock with the advancement/retreat operation of the driving shafts 60 and 61 for the up-and-down bend operation of the driving source unit 8B.

Thereby, like the first embodiment, the pinion gear 35a of the first rotary body 35 (or the pinion gear 36a of the second rotary body 36) rotates in interlock with the advancement/retreat operation of the working shaft 37, 38. When the pinion gear 35a (or 36a) rotates, the pulley 35b (or 36b) rotates together with the pinion gear 35a (or 36a). Consequently, in accordance with the rotational operation of the pulley 35b (or 36b), the wire 14 that is wound around the pulley 35b (or 36b) is pulled toward the driving source unit 8B. With the pulling operation of the wire 14, the bend section 10 is bend-operated.

Even in the above-described structure, the driving force transmission means 34 that is built in the large-diameter section 15 of the scope section 8A of the detachable-type endoscope 1 has the same structure as in the detachable-type endoscope 1 according to the first embodiment. Therefore, the same advantageous effects as with the first embodiment can be obtained.

Figure 11:
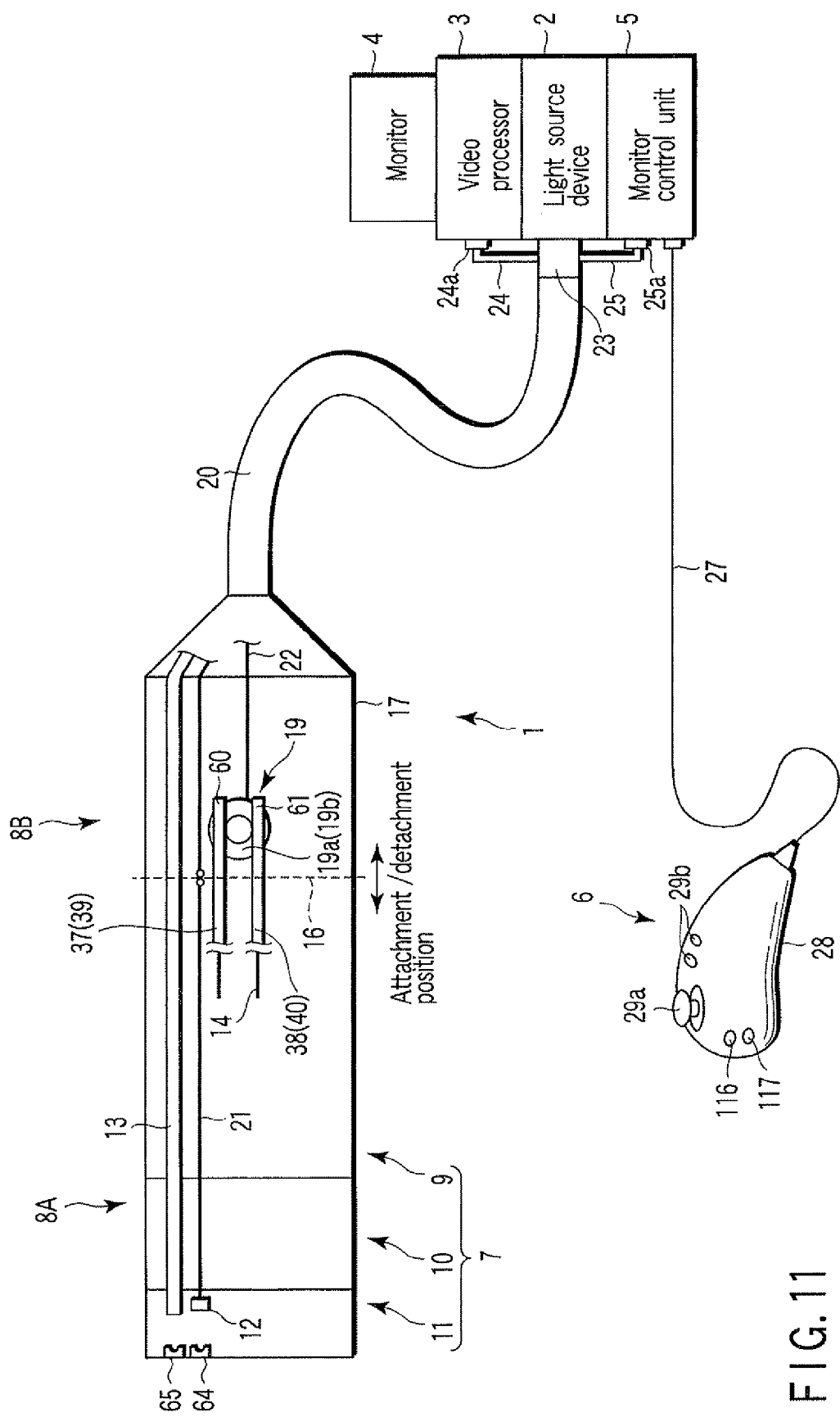
FIG. 11 schematically shows the structure of the entire system of a detachable-type endoscope according to a fifth embodiment of the present invention.

FIG. 11 schematically shows the structure of the entire system of a detachable-type endoscope 1 according to a fifth embodiment of the present invention. In this embodiment, the structure of the scope section 8A of the detachable-type endoscope 1 according to the first embodiment (see FIG. 1 to FIG. 7B) is altered as described below. The other structural parts are the same as those of the detachable-type endoscope 1 according to the first embodiment. The parts common to those of the detachable-type endoscope 1 according to the first embodiment are denoted by like reference numerals, and a description thereof is omitted.

Specifically, in this embodiment, tubes in the insertion section 7 of the scope section 8A in the first embodiment, such as the therapeutic device insertion tube 112, water feed tube 113 and air feed tube 114, are dispensed with.

The handpiece 28 of the operation unit 6 is provided with a joystick 29a for remotely bend-operating the bend section 10 and other remote switches 29b.

By operating the joystick 29a of the handpiece 28, the bend section 10 is remotely bend-operated. In addition, the endoscope operations corresponding to the functions of the remote switches 29b are performed by operating the remote switches 29b.

Needless to say, the present invention is not limited to the above-described embodiments, and various modifications may be made without departing from the spirit of the invention.

Next, other characteristic technical items of the present invention are described below.

Note (Item 1) An endoscope apparatus in which an operation section for performing a bend operation and a scope section, which includes a distal end section, a bend section, an insertion section and a coupling section for coupling to the operation section, are detachably coupled, characterized in that a pinion, which is integrally provided with a winding member for winding up a wire, is rotatably provided in the coupling section, and the bend operation is performed by rotating the pinion by axial movement of a pair of shaft members which are provided with racks that are opposed to the pinion.

(Item 2) The endoscope apparatus according to item 1, characterized in that a guide member which guides the pair of shaft members is provided.

(Item 3) The endoscope apparatus characterized in that the guide member according to item 2 is constituted by a guide member which is configured such that slits extending in a direction of movement are provided on sides opposite to the racks of the pair of shaft members, and projection portions engaging with the slits are provided.

(Item 4) The endoscope apparatus characterized in that the guide member according to item 2 is constituted by a guide member which is configured such that end portions projecting toward the pinion from the rack portions of the pair of shaft members are provided, and the end portions of the pair of shaft members are slidably guided.

(Item 5) The endoscope apparatus according to item 1, characterized in that a slack prevention member, which prevents slacking of the wire from the wire winding member, is provided.

(Item 6) The endoscope apparatus according to item 1, characterized in that an interference prevention member for preventing interference between the wire and the pair of shaft members is provided.

(Item 7) The endoscope apparatus according to item 1, characterized in that the insertion section has a hard or soft insertion section body.

(Item 8) An endoscope characterized by comprising: an insertion section which includes a bend section that is constituted by coupling a plurality of bend pieces and is insertable in a body cavity; a proximal section which is provided on a proximal end side of the insertion section; a main body section which is attachable/detachable to/from the proximal section; operation means which is provided in the main body section and is operable in a linear direction; an operation member which is provided in the main body section and is linearly operable in accordance with an operation of the operation means; a rotary body which is provided in the proximal section and converts linear movement of the operation member to rotational movement; and a wire which has a distal end portion connected to the bend section, is wound around the rotary body, and bends the bend section in accordance with an amount of winding.

(Item 9) An endoscope characterized by comprising: an insertion section which includes a bend section that is constituted by coupling a plurality of bend pieces and is insertable in a body cavity; a proximal section which is provided on a proximal end side of the insertion section; a main body section which is attachable/detachable to/from the proximal section; rotary means which is provided in the main body section and is rotationally operable; a first operation member which is provided in the main body section and linearly operates in accordance with rotation of the rotary means; a second operation member which is provided in the proximal section and linearly operates in accordance with an operation of the first operation member; a rotary body which is provided in the proximal section and converts linear movement of the second operation member to rotational movement; and a wire which has a distal end portion connected to the bend section, is wound around the rotary body, and bends the bend section in accordance with an amount of winding.

(Item 10) The endoscope according to item 9, characterized by including a second operation member which has an abutment portion that abuts on the first operation member and linearly operates by a pushing force at a time when the first operation member linearly operates.

(Item 11) The endoscope according to item 9, characterized by including a second operation member which has an engaging portion that is engaged with the first operation member, and is operated by transmission of linear movement of the first operation member.

(Item 12) The endoscope according to item 8 or 9, characterized in that a rack portion is formed on the operation member or the second operation member, and a pinion, which is meshed with the rack portion and rotates in accordance with advancement/retreat of the rack portion, is formed on the rotary body.

The present invention is effective in a technical field in which use is made of an endoscope of a driving source unit detachable type, wherein a driving source unit incorporating driving force generating means for bend-operating a bend section, which is disposed on a distal end side of an insertion section of the endoscope, is detachably coupled to a proximal section of the insertion section via an attachment/detachment section, and in a technical field of manufacture of this endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   a scope unit; and
   a driving source unit configured to be coupled to and detached from the scope unit,
   wherein the scope unit includes:
   an insertion section including a distal end portion and a proximal end portion and configured to be inserted into a body;
   a bend section provided in the distal end portion of the insertion section and configured to be bent;
   a scope unit coupling section provided on the proximal end portion of the insertion section;
   an operation member including a middle portion, a first end side portion and a second end side portion wherein the first end side portion includes a first distal end portion coupled to the bend section and is configured to be moved in an advance direction and a retreat direction opposite to each other and configured to operate the bend section to be bent in interlock with movement of the first end side portion in the retreat direction, and the second end side portion includes a second end portion coupled to the bending portion and is configured to be moved in the advance direction and the retreat direction and configured to operate the bend section to be bent in interlock with movement of the second end side portion in the retreat direction;

a rotary member provided in the scope unit coupling section, configured to be rotationally moved in a first rotational direction and a second rotational direction opposite to each other and including a working pinion gear and a pulley wherein the middle portion of the operation member is wound around the pulley, the first end side portion of the operation member is configured to be moved in the retreat direction via the pulley and the middle portion of the operation member wound around the pulley in interlock with rotational movement of the rotary member in the second rotational direction and configured to be moved in the advance direction via the pulley and the middle portion of the operation member wound around the pulley in interlock with rotational movement of the rotary member in the first rotational direction, and the second end side portion of the operation member is configured to be moved in the retreat direction via the pulley and the middle portion of the operation member wound around the pulley in interlock with rotational movement of the rotary member in the first rotational direction and configured be moved in the advance direction via the pulley and the middle portion of the operation member wound around the pulley in interlock with rotational movement of the rotary member in the second rotational direction;

a first working member provided in the scope unit coupling section, configured to be linearly moved in the advance direction and the retreat direction and including a first working abutment portion and a first working rack wherein the first working rack is meshed with the working pinion gear, the rotary member is configured to be rotationally moved in the first rotational direction via the working pinion gear and the first working rack meshed with each other in interlock with linear movement of the first working member in the advance direction, and the first working member is configured to be linearly moved in the retreat direction via the working pinion gear and the first working rack meshed with each other in interlock with rotational movement of the rotary member in the second rotational direction; and a second working member provided in the scope unit coupling section, configured to be linearly moved in the advance direction and the retreat direction and including a second working abutment portion and a second working rack wherein the second working rack is opposite to the first working rack relative to the working pinion gear and meshed with the working pinion gear, the rotary member is configured to be rotationally moved in the second rotational direction via the working pinion gear and the second working rack meshed with each other in interlock with linear movement of the second working member in the advance direction, and the second working member is configured to be linearly moved in the retreat direction via the working pinion gear and the second working rack meshed with each other in interlock with rotational movement of the rotary member in the first rotational direction; and the driving source unit includes:

a driving source unit coupling section configured to be coupled to and detached from the scope unit coupling section;
a first driving member provided in the driving source unit coupling section, configured to be linearly moved in the advance direction and the retreat direction and including a first driving abutment portion wherein the first working abutment portion is configured to be abutted on the first driving abutment portion, and the first working member is configured to be linearly moved in the advance direction via the first working abutment portion and the first driving abutment portion abutted on each other in interlock with linear movement of the first driving member in the advance direction, when the driving source unit coupling section is coupled to the scope unit coupling section;
a second driving member provided in the driving source unit coupling section, configured to be linearly moved in the advance direction and the retreat direction and including a second driving abutment portion wherein the second working abutment portion is configured to be abutted on the second driving abutment portion, and the second working member is configured to be linearly moved in the advance direction via the second working abutment portion and the second driving abutment portion abutted on each other in interlock with linear movement of the second driving member in the advance direction, when the driving source unit coupling section is coupled to the scope unit coupling section: and
a driving force generating mechanism configured to linearly move the first driving member in the advance direction and the retreat direction and linearly move the second driving member in an opposite direction to a direction of linear movement of the first driving member.

2. The endoscope according to claim 1,
wherein the driving force generating mechanism includes a driving pinion gear configured to be rotationally driven in the first rotational direction and the second rotational direction,
the first driving member includes a first driving rack meshed with the driving pinion gear, and the first driving member is configured to be linearly moved in the advance direction via the first driving rack and the driving pinion gear meshed with each other in interlock with rotational driving of the driving pinion gear in the first rotational-direction and configured to be linearly moved in the retreat direction via the first driving rack and the driving pinion gear meshed with each other in interlock with rotational driving of the driving pinion gear in the second rotational direction, and
the second driving member includes a second driving rack opposite to the first driving rack relative to the driving pinion gear and meshed with the driving pinion gear, and second driving member is configured to be linearly moved in the advance direction via the second driving rack and the driving pinion gear meshed with each other in interlock with rotational driving of the driving pinion gear in the second rotational direction and configured to be linearly moved in the retreat direction via the second driving rack and the driving pinion gear meshed with each other in interlock with rotational driving of the driving pinion gear in the first rotational direction.

3. An endoscope comprising:
a scope unit; and
a driving source unit configured to be coupled to and detached from the scope unit,
wherein the scope unit includes:

an insertion section including a distal end portion and a proximal end portion and configured to be inserted into a body;
a bend section provided in the distal end portion of the insertion section and configured to be bent;
a scope unit coupling section provided on the proximal end portion of the insertion section;
an operation member including a middle portion, a first end side portion and a second end side portion wherein the first end side portion includes a first distal end portion coupled to the bend section and is configured to be moved in an advance direction and a retreat direction opposite to each other and configured to operate the bend section to be bent in interlock with movement of the first end side portion in the retreat direction, and the second end side portion includes a second end portion coupled to the bending portion and is configured to be moved in the advance direction and the retreat direction and configured to operate the bend section to be bent in interlock with movement of the second end side portion in the retreat direction;
a rotary member provided in the scope unit coupling section, configured to be rotationally moved in a first rotational direction and a second rotational direction opposite to each other and including a working pinion gear and a pulley wherein the middle portion of the operation member is wound around the pulley, the first end side portion of the operation member is configured to be moved in the retreat direction via the pulley and the middle portion of the operation member wound around the pulley in interlock with rotational movement of the rotary member in the second rotational direction and configured to be moved in the advance direction via the pulley and the middle portion of the operation member wound around the pulley in interlock with rotational movement of the rotary member in the first rotational direction, and the second end side portion of the operation member is configured to be moved in the retreat direction via the pulley and the middle portion of the operation member wound around the pulley in interlock with rotational movement of the rotary member in the first rotational direction and configured be moved in the advance direction via the pulley and the middle portion of the operation member wound around the pulley in interlock with rotational movement of the rotary member in the second rotational direction;
a working member provided in the scope unit coupling section and configured to be linearly moved in the advance direction and the retreat direction and including a working abutment portion;
a transmission mechanism configured to rotationally move the rotary member in the first rotational direction in interlock with linear movement of the working member in the advance direction and configured to rotationally move the rotary member in the second rotational direction in interlock with linear movement of the working member in the retreat direction; and
an urging member configured to linearly urge the working member in the retreat direction, and
the driving source unit includes:
a driving source unit coupling section configured to be coupled to and detached from the scope unit coupling section;
a driving member provided in the driving source unit coupling section, configured to be linearly moved in the advance direction and the retreat direction and including a driving abutment portion wherein the working abutment portion is configured to be abutted on the driving abutment portion, the working member is configured to be linearly moved in the advance direction via the working abutment portion and the driving abutment portion abutted on each other in interlock with linear movement of the driving member in the advance direction, and the working member is configured to be linearly moved in the retreat direction by the urging member in interlock with linear movement of the driving member in the retreat direction, when the driving source unit coupling section is coupled to the scope unit coupling section; and a driving force generating mechanism configured to linearly move the driving member in the advance direction and the retreat direction.

4. The endoscope according to claim 3, wherein the transmission mechanism includes:
 a working pinion gear provided in the rotary member; and
 a working rack provided in the working member and meshed with the working pinion gear.

5. An endoscope comprising:
 a scope unit; and
 a driving source unit configured to be coupled to and detached from the scope unit,
 wherein the scope unit includes:
 an insertion section including a distal end portion and a proximal end portion and configured to be inserted into a body;
 a bend section provided in the distal end portion of the insertion section and configured to be bent:
 a scope unit coupling section provided on the proximal end portion of the insertion portion:
 an operation member including a middle portion, a first end side portion and a second end side portion wherein the first end side portion includes a first distal end portion coupled to the bend section and is configured to be moved in an advance direction and a retreat direction opposite to each other and operate the bend section to be bent in interlock with movement of the first end side portion in the retreat direction, and the second end side portion includes a second end portion coupled to the bending portion and is configured to be moved in the advance direction and the retreat direction and operate the bend section to be bent in interlock with movement of the second end side portion in the retreat direction;
 a rotary member provided in the scope unit coupling section, configured to be rotationally moved in a first rotational direction and a second rotational direction opposite to each other and including a working pinion gear and a pulley wherein the middle portion of the operation member is wound around the pulley, the first end side portion of the operation member is configured to be moved in the retreat direction via the pulley and the middle portion of the operation member wound around the pulley in interlock with rotational movement of the rotary member in the second rotational direction and configured to be moved in the advance direction via the pulley and the middle portion of the operation member wound around the pulley in interlock with rotational movement of the rotary member in the first rotational direction, and the second end side portion of the operation member is configured to be moved in the retreat direction via the pulley and the middle portion of the operation member wound around the pulley in interlock with rotational movement of the rotary member in the first rotational direction and configured be moved in the advance direction via the pulley and the middle portion of the operation member wound around the pulley in interlock with rotational movement of the rotary member in the second rotational direction;

a working member provided in the scope unit coupling section, configured to be linearly moved in the advance direction and the retreat direction and including a working engagement portion; and a transmission mechanism configured to rotationally move the rotary member in the first rotational direction in interlock with linear movement of the working member in the advance direction and configured to rotationally move the rotary member in the second rotational direction in interlock with linear movement of the working member in the retreat direction, and the driving source unit includes:

a driving source unit coupling section configured to be coupled to and detached from the scope unit coupling section;

a driving member provided in the driving source unit coupling section, configured to be linearly moved in the advance direction and the retreat direction and including a driving engagement portion wherein the working engagement portion is configured to be engaged with the driving engagement portion, the working member is configured to be linearly moved in the advance direction via the working engagement portion and the driving engagement portion engaged with each other in interlock with linear movement of the driving member in the advance direction, and the working member is configured to be linearly moved in the retreat direction via the working engagement portion and the driving engagement portion engaged with each other in interlock with linear movement of the driving member in the retract direction; and a driving force generating mechanism configured to linearly move the driving member in the advance direction and the retreat direction.

6. The endoscope according to claim 5, wherein the transmission mechanism includes:
 a working pinion gear provided in the rotary member; and
 a working rack provided in the working member and meshed with the working pinion gear.

* * * * *